(12) United States Patent
Yanuma

(10) Patent No.: US 9,295,819 B2
(45) Date of Patent: Mar. 29, 2016

(54) FLUID SUPPLY BODY AND BALLOON CATHETER

(71) Applicant: OLYMPUS CORPORATION, Tokyo (JP)

(72) Inventor: Yutaka Yanuma, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 87 days.

(21) Appl. No.: 13/944,555

(22) Filed: Jul. 17, 2013

(65) Prior Publication Data

US 2014/0031746 A1    Jan. 30, 2014

Related U.S. Application Data

(60) Provisional application No. 61/676,463, filed on Jul. 27, 2012.

(51) Int. Cl.
*A61M 25/10*    (2013.01)

(52) U.S. Cl.
CPC ..... *A61M 25/1018* (2013.01); *A61M 25/10184* (2013.11); *A61M 25/10187* (2013.11)

(58) Field of Classification Search
CPC .................. A61M 25/1018; A61M 25/10184; A61M 25/10187
USPC ......... 604/187, 220, 221, 222, 224, 227–229, 604/97.01, 97.02, 97.03, 98.01, 99.01
See application file for complete search history.

(56) References Cited

U.S. PATENT DOCUMENTS

| 1,589,046 | A | * | 6/1926 | Brix | 604/227 |
| 1,798,116 | A | * | 3/1931 | Brockway | 604/220 |
| 2,882,901 | A | * | 4/1959 | De Venezia | 604/227 |
| 6,267,717 | B1 | | 7/2001 | Stoll et al. | |
| 2009/0234281 | A1 | * | 9/2009 | Yanuma | 604/97.02 |

* cited by examiner

*Primary Examiner* — Manuel Mendez
(74) *Attorney, Agent, or Firm* — Oliff PLC

(57) ABSTRACT

A fluid supply body for supplying a fluid to a balloon formed of a material having elasticity and inflating the balloon, the fluid supply body includes a cylinder, a plunger, an adjusting portion that is attached to the plunger and adjusts the movement amount of the plunger so that the balloon is inflated with to a predetermined inflation diameter, and a fixing portion that is provided at the cylinder and fixes the plunger at a position within the cylinder corresponding to the movement amount adjusted by the adjusting portion, wherein the adjusting portion has a plurality of engaging portions that specify movement amounts corresponding to a plurality of different inflation diameters of the balloon, and the fixing portion has an engaged portion, and a converting portion.

8 Claims, 17 Drawing Sheets

FLUID SUPPLY BODY AND BALLOON CATHETER

CROSS-REFERENCE TO RELATED APPLICATION

This application is entitled to the benefit of Provisional Patent Application No. 61/676,463, filed Jul. 27, 2012.

BACKGROUND OF THE INVENTION

1. Field of the Invention

The present invention relates to a fluid supply body and a balloon catheter for supplying a fluid to a balloon.

2. Description of Related Art

Generally; in the medical field, medical catheters with a balloon for the urinary organs, such as a catheter for urethral indwelling, and various balloon catheters having a balloon in the vicinity of a catheter distal end portion, such as a tracheal tube, a catheter for the digestive organs, and a balloon catheter for heart pumping, are extensively used.

When the balloons of the balloon catheters become inflated, generally, a fluid supply body (for example, a medical syringe) is attached to a hand-side cap that is fluid-connected with a balloon portion, and a necessary amount of a fluid is injected into the fluid supply body to inflate a balloon (for example, refer to U.S. Pat. No. 6,267,717).

For example, in a case where a balloon is used when a gallstone is taken out through a bile duet the diameter of a bile duct outlet is small. Therefore, if the diameter of the balloon is not made small the balloon cannot be pulled out of the bile duet. Thus, usually, a helper operates the fluid supply body in synchronization with the operation of an operator who pulls out the balloon, and a pull-out operation is performed while deflating the balloon.

SUMMARY OF THE INVENTION

According to a first aspect of the present invention, a fluid supply body for supplying a fluid to a balloon formed of a material having elasticity and inflating the balloon, the fluid supply body includes a cylinder that is a tubular shape having a first opening and a second opening at both ends thereof, and that contains the fluid, a plunger that is inserted into the cylinder from the second opening so as to be able to advance and retract in a direction of an axis of the cylinder and that pushes out the fluid which is in the cylinder from the first opening to the outside of the cylinder, an adjusting portion that is attached to the plunger and adjusts the movement amount of the plunger so that the balloon is inflated to a predetermined inflation diameter, and a fixing portion that is provided at the cylinder and fixes the plunger at a position within the cylinder corresponding to the movement amount adjusted by the adjusting portion. The inflation diameter is changed as the balloon is inflated, the adjusting portion has a plurality of engaging portions that specify movement amounts corresponding to a plurality of different inflation diameters of the balloon, and the fixing portion has an engaged portion that is engaged to the engaging portions and fixes the plunger, and a converting portion that has a first finger-hooked portion disposed relatively on a front side in a direction in which the plunger is pushed into the cylinder, and a second finger-hooked portion disposed relatively on a rear side in the direction in which the plunger is pushed into the cylinder, and that converts a force applied to the first finger-hooked portion when the plunger is pulled out of the cylinder into a force that releases the engagement of the engaging portions to the engaged portion.

According to a second aspect of the present invention, in the fluid supply body according to the first aspect the fixing portion may have a flat spring portion that has the engaged portion formed at the first end thereof and has elasticity; and an attaching portion to which the second end of the flat spring portion is fixed and the cylinder is attached, the first finger-hooked portion may be fixed to the first end side in the flat spring portion, the second finger-hooked portion may be fixed to the attaching portion, and the first finger-hooked portion may be movable relative to the second finger-hooked portion.

According to a third aspect of the present invention, in the fluid supply body according to the second aspect, the first finger-hooked portion may be disposed at a position apart from the axis in a direction perpendicular to the axis of the cylinder, and the flat spring portion may be disposed at a position further apart from the first finger-hooked portion with respect to the axis.

According to a fourth aspect of the present invention, in the fluid supply body according to the second aspect, an end of the flat spring portion, which is relatively located on the rear side in the direction in which the plunger is pushed into the cylinder, may be fixed to the attaching portion, extend to the front side in the direction in which the plunger is pushed into the cylinder, and the engaged portion may be formed on an end on the front side.

According to a fifth aspect of the present invention, in the fluid supply body according to the first aspect, the adjusting portion may have a shaft portion that extends parallel to the axis of the cylinder and at which the plurality of engaging portions are provided, a coupling portion that couples the shaft portion and the plunger, and a ring portion that is provided at the coupling portion, the fixing portion may have a tubular attaching portion to which the cylinder is attached, and a stopper that is attached to the attaching portion, rotates around the axis of the cylinder, and has a plurality of wall portions that comes into contact with the end portion of the shaft portion, and the plurality of wall portions may be positioned at mutually different positions in the direction of the axis of the cylinder, and are arranged side by side in a circumferential direction of the cylinder.

According to a sixth, aspect of the present invention, a balloon catheter having a balloon formed of a material having elasticity, may include the fluid supply body according to any one of the first aspect to the fifth aspect.

According to a seventh aspect of the present invention, a fluid supply body for supplying a fluid to a balloon formed of a material having elasticity and inflating the balloon, the fluid supply body includes a cylinder that is formed in a tubular shape having a first opening and a second opening at both ends thereof and that contains the fluid, a plunger that is inserted into the cylinder from the second opening so as to be able to advance and retract in a direction of an axis of the cylinder and that pushes out the fluid which is in the cylinder from the first opening to the outside of the cylinder, an adjusting portion that is attached to the plunger and adjusts the movement amount of the plunger so that the balloon is inflated with a predetermined inflation diameter, a fixing portion that is provided at the cylinder and fixes the plunger at a position within the cylinder corresponding to the movement amount adjusted by the adjusting portion, and a stopper that is provided in a state where a position of the stopper is fixed with respect to the cylinder and that is capable of coming into contact with the adjusting portion. The adjusting portion has a plurality of engaging portions that specify movement, amounts corresponding to a plurality of different inflation diameters of the balloon, and the fixing portion has an engaged portion that is engaged to the engaging portions and fixes the plunger.

According to an eighth aspect of the present invention, in the fluid supply body according to the seventh aspect, the adjusting portion may have a shaft portion that extends parallel to the axis of the cylinder and at which the plurality of engaging portions are provided, a coupling portion that couples the shaft portion and the plunger, and a ring portion that is provided at the coupling portion, the fixing portion may have a tubular attaching portion to which the cylinder is attached, the stopper may be attached to the attaching portion, rotate around the axis of the cylinder, and have a plurality of wall portions that abut against the end portion of the shaft portion, and the plurality of wall portions may be positioned at mutually different positions in the direction of the axis of the cylinder, and be arranged side by side in a circumferential direction of the cylinder.

DETAILED DESCRIPTION OF THE INVENTION

A first embodiment of the present invention will be described below.

Figure 1:
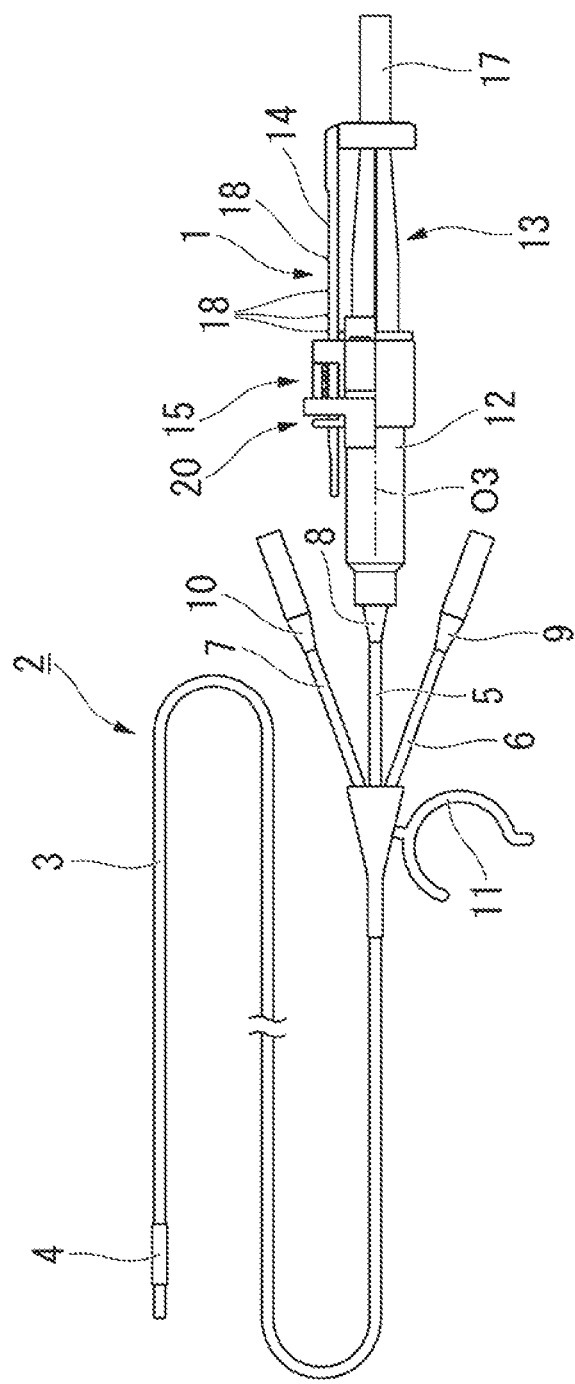
FIG. 1 is a view showing a balloon catheter including a fluid supply body of a first embodiment of the present invention.

FIG. 1 is a view showing a balloon catheter including a fluid supply body of the present embodiment. As shown in FIG. 1, the balloon catheter 2 is configured so as to include a long sheath 3 having flexibility, a balloon 4 attached to the vicinity of a distal end of the sheath 3, and a fluid supply body 1 attached to a proximal end of the sheath 3.

The sheath 3 is formed of materials having flexibility, such as resin, and has three lumens of a first lumen 5 for supplying a fluid to the balloon 4, a second lumen 6 through which a guide wire for guiding the distal end of the balloon catheter 2 to a desired part within a patient's body cavity is inserted, and a third lumen 7 for feeding various liquids, such as a contrast medium, into the patient's body cavity.

A distal end of the first lumen 5 passes through an outer peripheral surface of the sheath 3, and opens to the balloon 4. Distal ends of the second lumen 6 and the third lumen 7 open to the distal end of the sheath 3. The distal ends of the second lumen 6 and the third lumen 7 may open at positions other than at the distal end of the sheath 3.

The respective lumens 5, 6, and 7 do not communicate with each other, are provided within the sheath 3 in an independent state, extend independently at proximal ends thereof, respectively, and are formed with three ports of a first port 8, a second port 9, and a third port 8, respectively. The fluid supply body 1 is connected to the first port 10.

Additionally, a holder 11 for fixing the balloon catheter 2 to an endoscope device or the like is provided at the proximal end of the sheath 3.

The balloon 4 is formed of materials having elasticity, and is configured so as to inflate while increasing its diameter gradually as fluids, such as a liquid and a gas, supplied front the fluid supply body 1 stagnates within the balloon. That is, the inflation diameter is changed as the balloon is inflated. As the materials of the balloon 4, for example, materials such as crude rubber, synthetic rubber, polyurethane, polyamide-based elastomer, and silicon can be favorably adopted.

Figure 2:
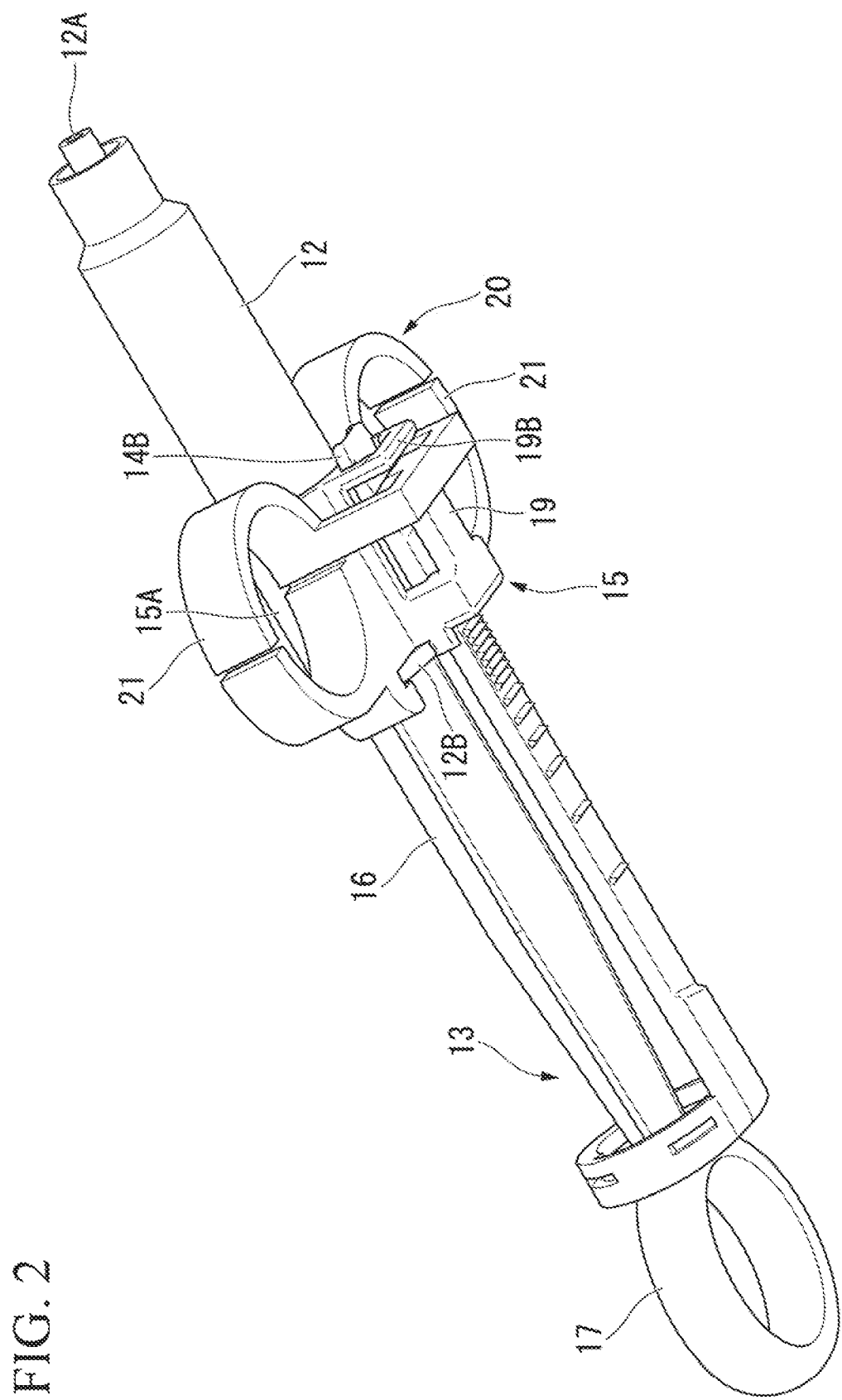
FIG. 2 is a perspective view of the fluid supply body.
Figure 3:
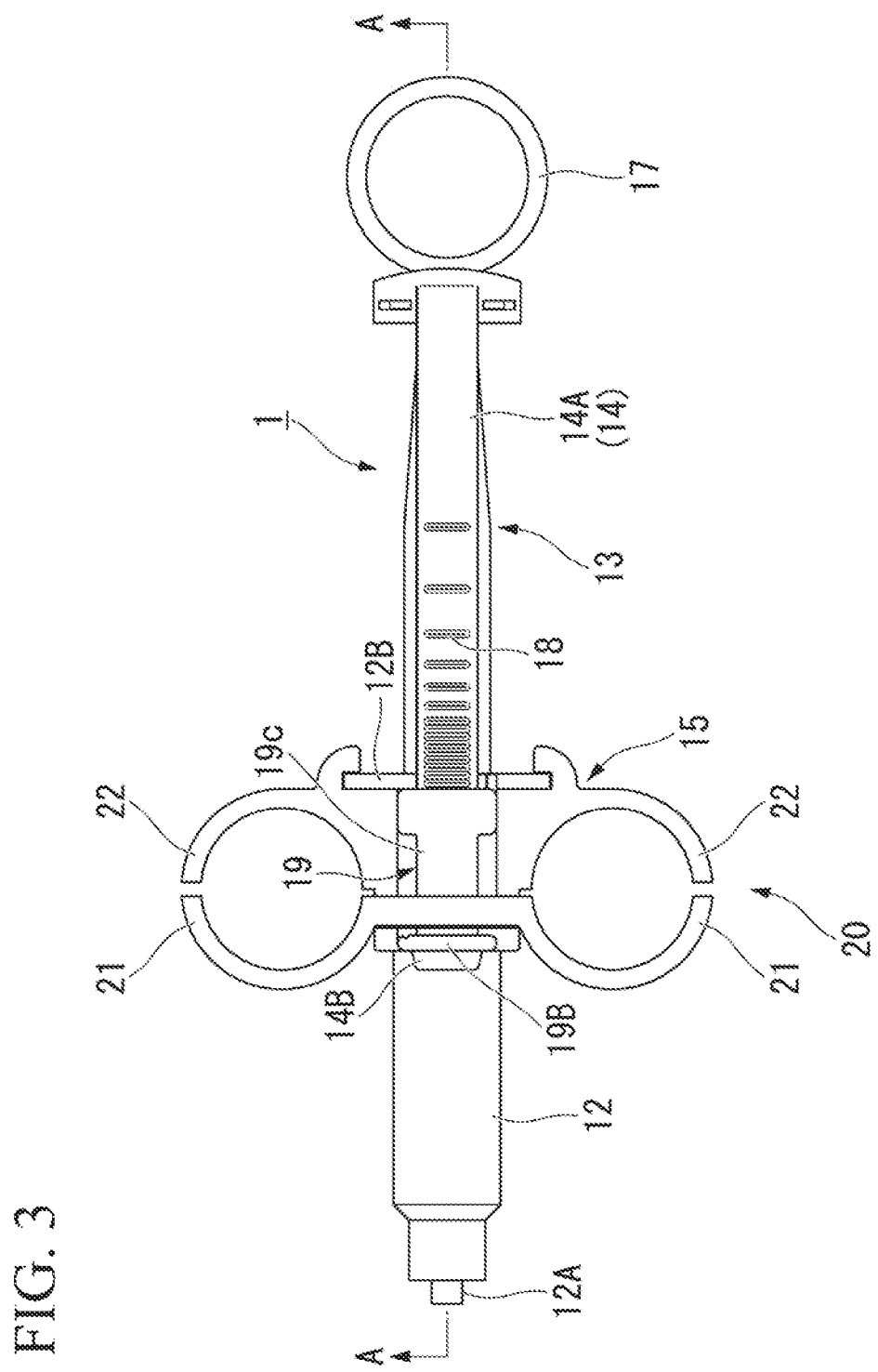
FIG. 3 is a plan view of the fluid supply body.
Figure 4:
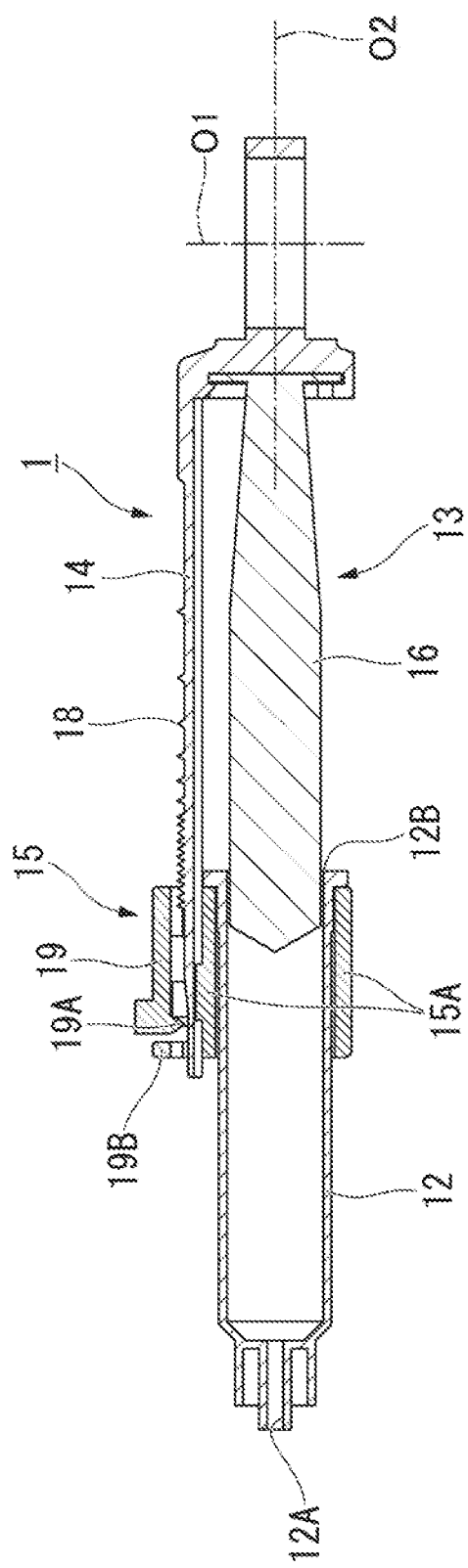
FIG. 4 is a cross-sectional view in line A-A of FIG. 3.
Figure 5:
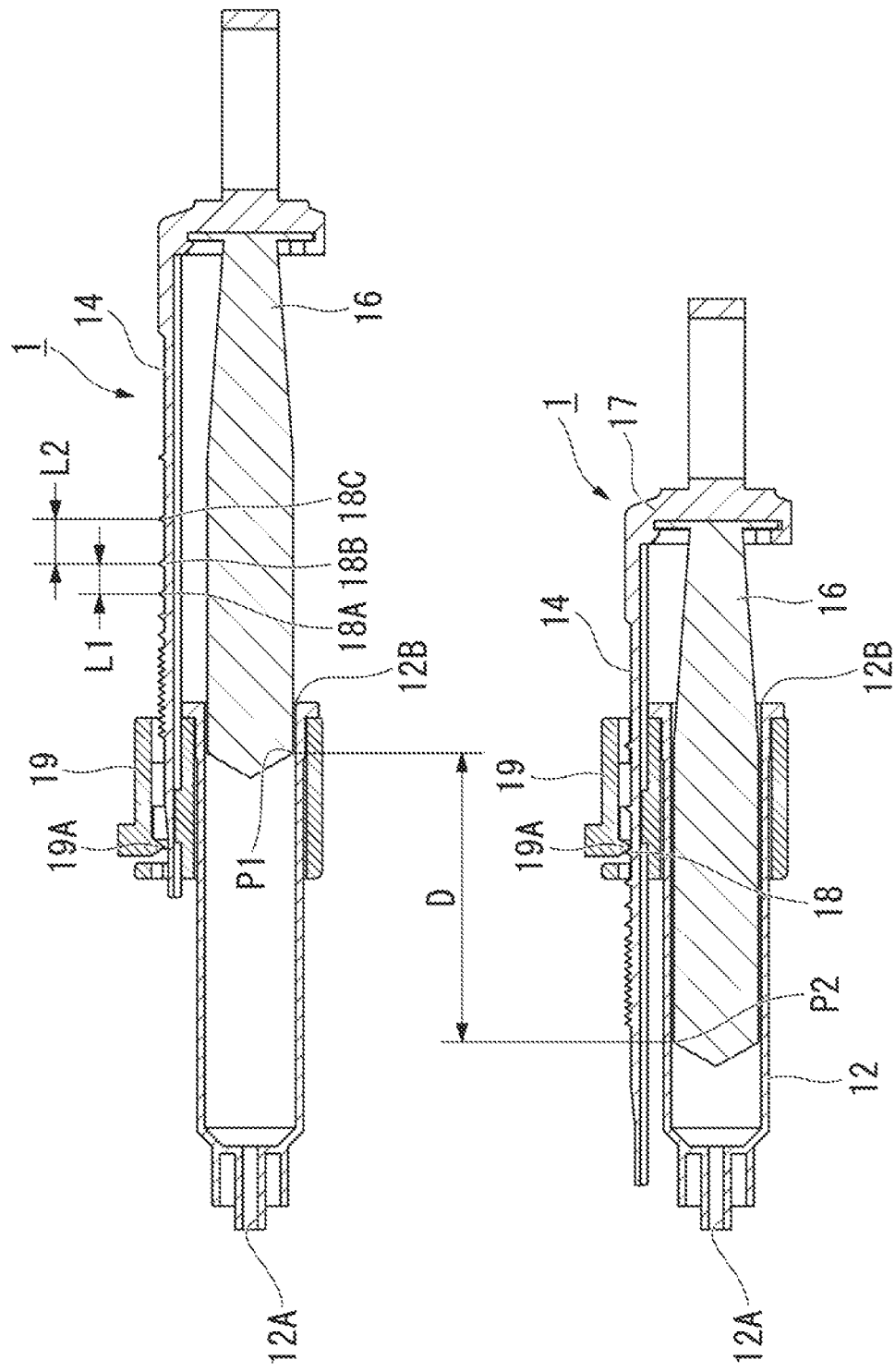
FIG. 5 is a view showing the movement and movement amount of a plunger.

FIG. 2 is a perspective view of the fluid supply body 1, FIG. 3 is a plan view of the fluid supply body 1, FIG. 4 is a cross-sectional view in line A-A of FIG. 3, and FIG. 5 is a cross-sectional view for describing a positional relationship when a plunger 13 advances and retracts with respect to a cylinder 12.

As shown in FIGS. 2 to 4, the fluid supply body 1 is configured so as to include the cylindrical cylinder 12, the plunger 13 inserted through the cylinder 12, an adjusting portion 14 attached to the plunger 13, and a fixing portion 15 attached to the cylinder 12.

The cylinder 12 is formed in a cylindrical shape, and a fluid is contained in an inner cavity of the cylinder. The fluid to be contained may be a gas such as air or may be a liquid such as a physiological salt solution. In the cylinder 12, a first end portion 12A on a distal end side and a second end portion 12B on a proximal end side open respectively. The first end portion 12A has a shape capable of being connected with the first port 8 by fitting into the first port 8 shown in FIG. 1.

As shown in FIG. 4, the plunger 13 has a main body 16 inserted into the cylinder 12, and a grip 17 provided on a proximal end side of the main body 16. A distal end side of the main body 16 is inserted into the inner cavity of the cylinder 12, and the main body 16 is adapted to be able to advance and retract in the cylinder 12 within the cylinder 12 in a longitudinal direction of the cylinder 12. The external diameter of the distal end of the main body 16 is approximately equal to the internal diameter of the cylinder 12, and if the main body 16 is moved toward the first end portion 12A of the cylinder 12 as shown in FIG. 5, a fluid in the cylinder 12 is pushed out of the first end portion 12A.

In addition, in the present embodiment, a general medical disposable syringe can be used as the cylinder 12 and the plunger 13. A configuration in which the cylinder 12 was molded integrally with the fixing portion 15 or a configuration in which the plunger 13 is molded integrally with the adjusting portion 14 can also be adopted.

The grip 17, which is apart on which a finger is hooked when a user operates the plunger 13, is formed in the shape of a ring. In the present embodiment, the grip 17 is formed in an annular shape such that a centerline O1 thereof is orthogonal to an axis O2 of the plunger 13.

The adjusting portion 14 is a plate-shaped member and has a shaft portion 14A extending substantially parallel to the main body 16 of the plunger 13, and a protruding portion 14B formed at a distal end of the shaft portion 14A.

As shown in FIGS. 3 and 4, the shaft portion 14A is formed in a plate shape, and a plurality of engaging projections 18 are formed on a surface which is opposite to a surface facing the main body 16, of both surfaces in the plate thickness direction, of the shaft portion 14A, in order to specify the movement amount of the plunger 13. The intervals of the respective engaging projections 18 are set so as to be longer as the projections are closer to a proximal end of the plunger 13. For example, as shown in FIG. 5, a distance L2 between an engaging projection 18B and an engaging projection 18C closer to the proximal end side than the engaging projection 18B is longer than a distance L1 between an engaging projection 18A and the engaging projection 18B closer to the proximal end side than the engaging projection 18A.

Figure 6:
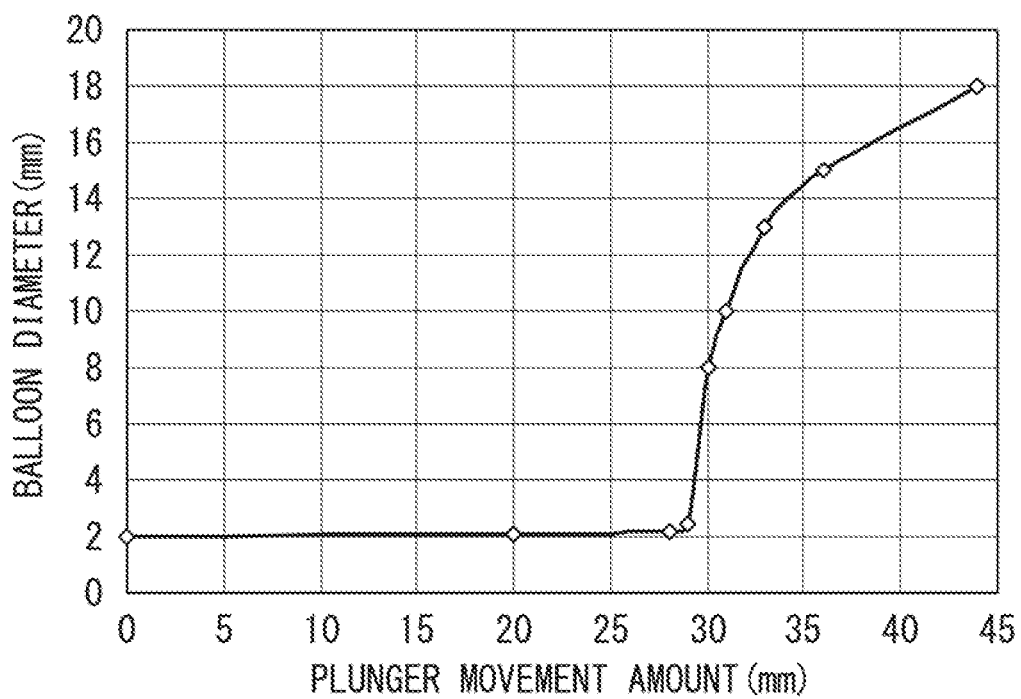
FIG. 6 shows an example of a graph showing the relationship between the diameter of a balloon and the movement amount of the plunger.

Distances between the respective engaging projections 18 are determined based on the characteristics of the balloon 4 that is a target to which the fluid supply body 1 supplies a fluid. FIG. 6 shows an example of a graph showing the relationship between the diameter of the balloon and the movement amount of the plunger 13.

In addition, the "movement amount" means a distance D between the same parts of the plunger 13 at a reference position P1 that is an initial position of the plunger 13 and at a point P2 to which the plunger 13 has moved, as shown in FIG. 5, in the fluid supply body 1 connected to the balloon catheter 2 in a state where the balloon 4 is deflated.

It is preferable if the reference position P1 of the plunger 13 is set so that the distal end of the plunger 13 is located in the vicinity of the second end portion 12B of the cylinder 12, since a wide range of movement amount can be taken. However, the reference position P1 may be arbitrary positions without being limited to this. In the present embodiment, the position of the plunger 13 where protruding portion 14B of the adjusting portion 14 comes into contact with a drop-off preventing portion of the fixing portion 15 to be described below is used as the reference position.

As shown in FIG. 6, the differential movement amount of the plunger 13 required in order to increase the diameter of the balloon 4 inflated to a desired diameter by a predetermined value, for example, 1 mm increase, becomes larger as the diameter of the balloon 4 before the diameter is increased. Accordingly; from the above description, it is understood that if the forming positions of the respective engaging projections 18 are set so that the distances (intervals) between adjacent engaging projections 18 become gradually longer as the diameter of the balloon 4 becomes larger, then the inflation diameters of the balloon 4 corresponding to the respective engaging projections 18 can be regular intervals, for example, intervals of 1 mm or the like. In addition, the forming positions of the engaging projections 18 may be appropriately set according to the elastic characteristics of the balloon 4, the control intervals of desired diameters of the balloon, the values of the diameters of the balloon to be inflated and maintained, or the like.

As shown in FIG. 3, since the protruding portion 14B is formed to protrude from the shaft portion 14A so as to be broader than the shaft portion 14A, the plunger 13 can be prevented from dropping out of the cylinder 12. Additionally, the protruding portion 14B is adapted to have a size such that the shaft portion 14A can be removed from the fixing portion 15 to be described below.

As shown in FIGS. 2 to 4, the fixing portion 15 has a cylindrical attaching portion 15A to which the cylinder 12 is attached, a engaged portion 19 that engages an engaging projection 18 of the adjusting portion 14, and a converting portion 20 for releasing the engagement state of the engaged portion 19 with respect to the engaging projection 18.

As shown in FIG. 4, the engaged portion 19 has a flat spring portion 19C located at outer side in the radial direction of the cylinder 12 than the engaging projections 18, and a projection 19A that is formed to protrude toward the engaging projections 18 from the flat spring portion 19C. The flat spring portion 19C is fixed, to the attaching portion 15A on the proximal end side, and extends toward the distal end side.

In the present embodiment, the flat spring portion 19C, which is a member that is more flexible than a first finger-hooked portion 21 (refer to FIG. 3) to be described below and has elasticity, is elastic-ally deformable so as to bend in a direction away from the central axis O2 of the plunger 13. The flat spring portion 19C may be formed of materials that are more flexible than the first finger-hooked portion 21, and may be flexible by being formed thinner or slimmer than the first finger-hooked portion 21.

If the plunger 13 slides in the cylinder 12 and the surface of an engaging projection 18 on the proximal end side and the surface of the projection 19A on the distal end side come into contact with each other, the positional relationship between the plunger 13 and the cylinder 12 is maintained, and the balloon 4 is maintained in a state where the balloon is inflated with a diameter corresponding to the movement amount of the plunger 13 specified by the engaging projection 18.

Additionally, as shown in FIGS. 2 and 3, the engaged portion 19 is provided with a frame-like drop-off preventing portion 19B, and the adjusting portion 14 is inserted through the drop-off preventing portion 19B. If the plunger 13 is pulled to the proximal end side, the protruding portion 14B of the adjusting portion 14 and the drop-off preventing portion 19B come into contact with each other in a place where the distal end of the plunger 13 has moved to the vicinity of the second end portion 12B of the cylinder 12, so that the plunger 13 cannot be moved to the proximal end side any more. This prevents the plunger 13 torn dropping out of the cylinder 12.

As shown in FIG. 3, the converting portion 20 has the first finger-hooked portion 21 that is relatively disposed on the front side in the direction in which the plunger 13 is pushed into the cylinder 12, and a second finger-hooked portion 22 that is relatively disposed on the rear side.

The first finger-hooked portion 21, which is a member having a semicircular dented shape that receives a user's finger, is fixed to the distal end side in the flat spring portion 19C, and operates integrally with the flat spring portion 19C. In the present embodiment, the first finger-hooked portions 21 are provided in two places apart from each other with the cylinder 12 interposed therebetween so that two fingers other than a user's thumb can be put thereto. In addition, a configuration may be adopted in which the first finger-hooked portion 21 and the flat spring portion 19C are integrally molded.

The second finger-hooked portion 22, which is a member having a semicircular dented shape that receives a user's finger, is fixed to the fixing portion 15. In the present embodiment, the second finger-hooked portions 22 are provided in two places apart from each other with the cylinder 12 interposed therebetween so that two fingers other than a user's thumb can be put thereto. In addition, a configuration may be adopted in which the second finger-hooked portion 22 and the fixing portion 15 are integrally molded.

In the present embodiment the first finger-hooked portion 21 and the second finger-hooked portion 22 are arranged side by side in the front-and-rear direction so that the first finger-hooked portion 21 and the second finger-hooked portion 22 are annular as a whole and so that a semicircle on the front side is the first finger-hooked portion 21 and a semicircle on the rear side is the second finger-hooked portion 22. The first finger-hooked portion 21 and the second finger-hooked portion 22 are arranged to have a clearance such that a user's fingers does not drop out from a gap between the first finger-hooked portion 21 and the second finger-hooked portion 22 or to come into contact with each other by the biasing force of the flat spring portion 19C.

As shown in FIG. 1, the first finger-hooked portion 21 and the second finger-hooked portion 22 are arranged at positions offset from an axis O3 of the cylinder 12. That is, the first finger-hooked portion 21 and the second finger-hooked portion 22 are disposed at positions apart from the axis O3 of the cylinder 52 in the direction perpendicular to the axis O3 of the cylinder 12. Additionally, the first finger-hooked portion 21 and the second finger-hooked portion 22 are arranged so as to be located at positions where the flat spring portion 19C are further apart from the first finger-hooked portion 21 and the second finger-hooked portion 22 with respect to the axis O3 of the cylinder 12.

The actions when the balloon catheter 2 configured as described above is used will be described below. First, an endoscope 120 (refer to FIGS. 7 and 13) is inserted into a patient's body cavity, and a distal end is moved to the vicinity of a tissue (the vicinity of a bile duct 110 in the present embodiment) of a treatment target (insertion step).

In parallel with this, the balloon catheter 2 is prepared in a usable state. A user pulls the plunger 13 of the fluid supply body 1 to the proximal end side, moves the plunger to the above-described reference position P1, and fills a fluid into the cylinder 12. Then, the first end portion 12A of the cylinder 12 is connected to the first port 8 (connection step; refer to FIG. 7).

Figure 7:
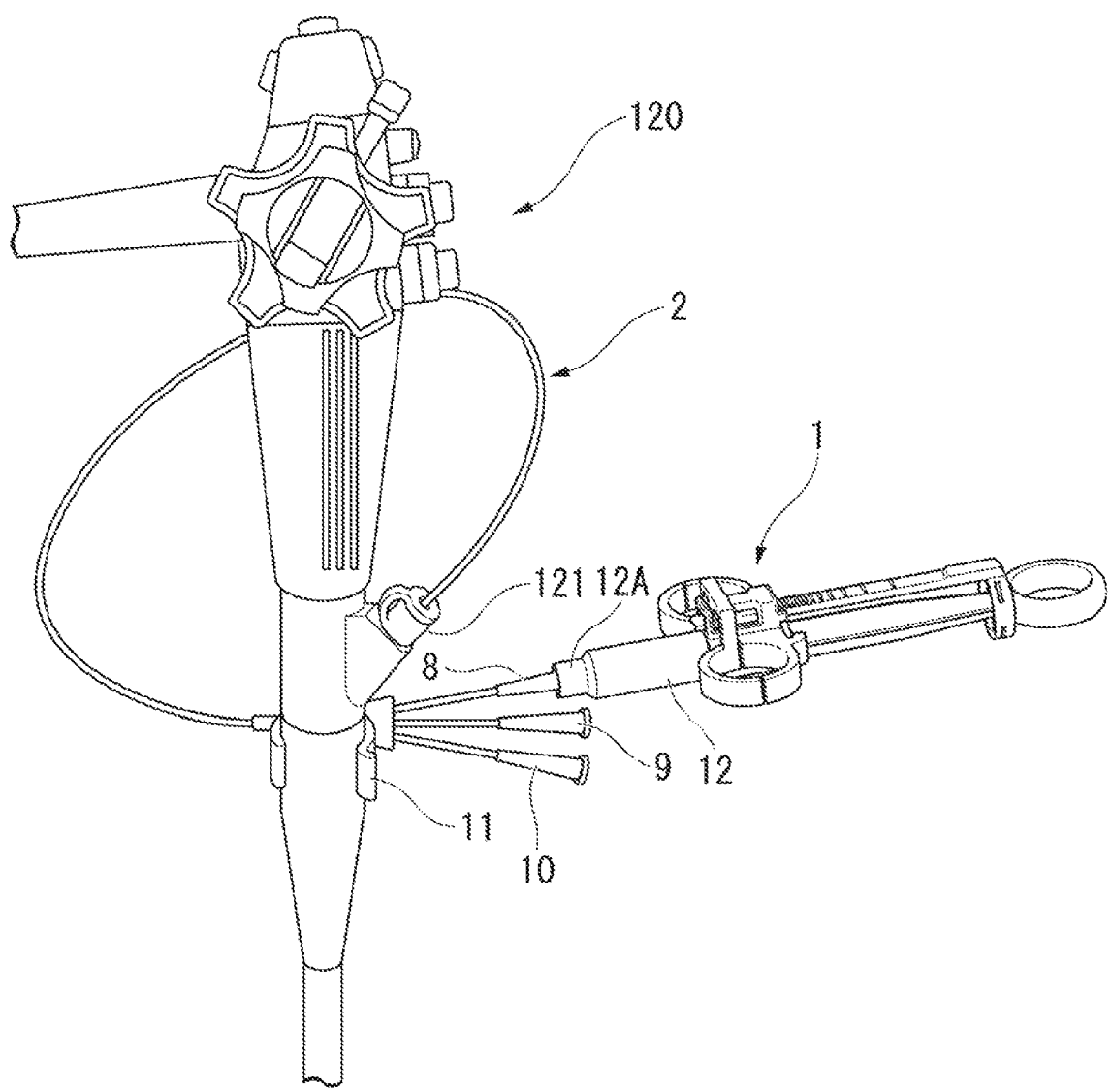
FIG. 7 is a view showing a state where the balloon catheter is attached to an endoscope.

The user inserts the distal end of the balloon catheter 2 into a working channel (not shown) in the endoscope from a forceps port 121 of the endoscope 120, and causes the distal end of the balloon catheter 2 to protrude from the distal end of the endoscope 120. Although a helper stands by the user and operates the fluid supply body 1 usually, a handle of the balloon catheter 2 may also be fixed to the endoscope 120 through the holder 11, as shown in FIG. 7, and the user himself/herself may operate the fluid supply body 1.

Figure 13A:
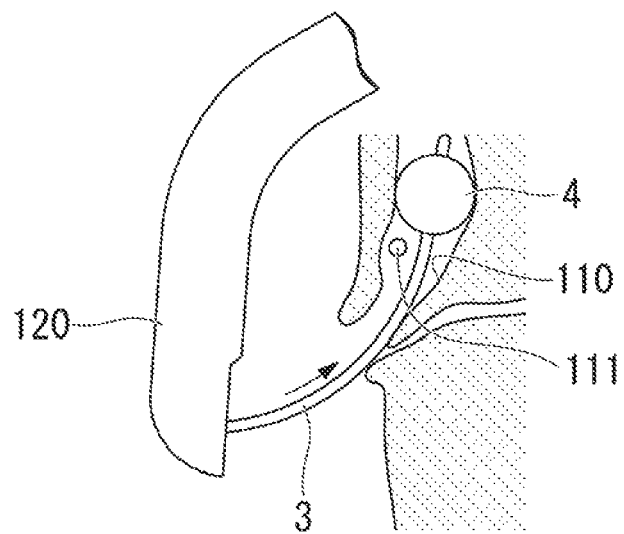
FIG. 13A is a view showing a state where a gallstone is removed.

For example, the user inserts the sheath 3 into the bile duet 110 (refer to FIG. 13 (a)) in a state where the balloon 4 is deflated, and arranges the balloon 4 so that the balloon 4 is located on a distal side of the gallstone 110. Thereafter, the user inflates the balloon 4.

When inflating the balloon 4, first, the user passes his/her finger through the grip 17 of the plunger 13, and hooks his/her fingers on the first finger-hooked portion 21 and the second finger-hooked portion 22. In the present embodiment, it is preferable that the respective fingers be hooked in a positional relationship where the user's palm faces the surface of the adjusting portion 14 on which the engaging projections 18 are formed.

Figure 8:
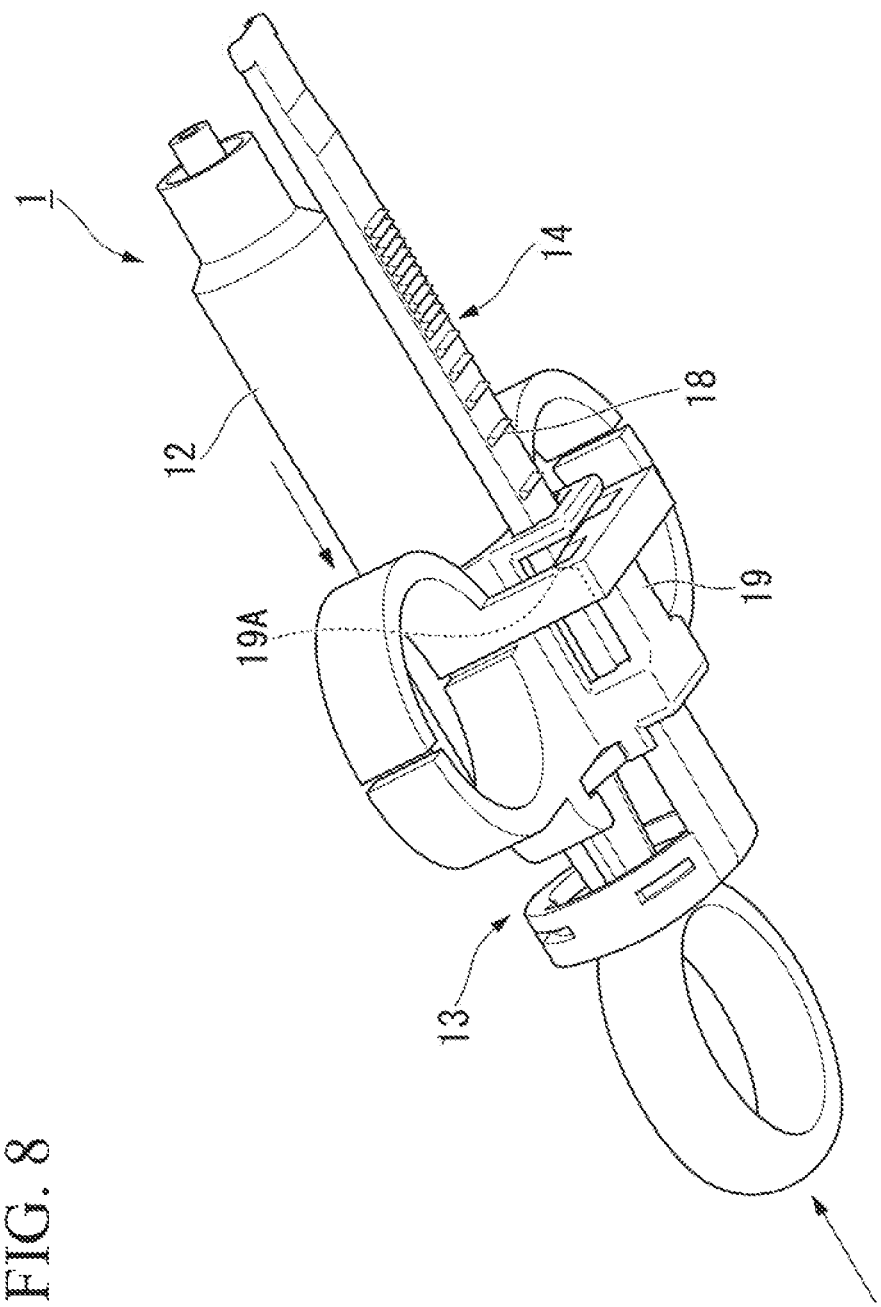
FIG. 8 is a view showing an action when the fluid supply body is used.
Figure 9:
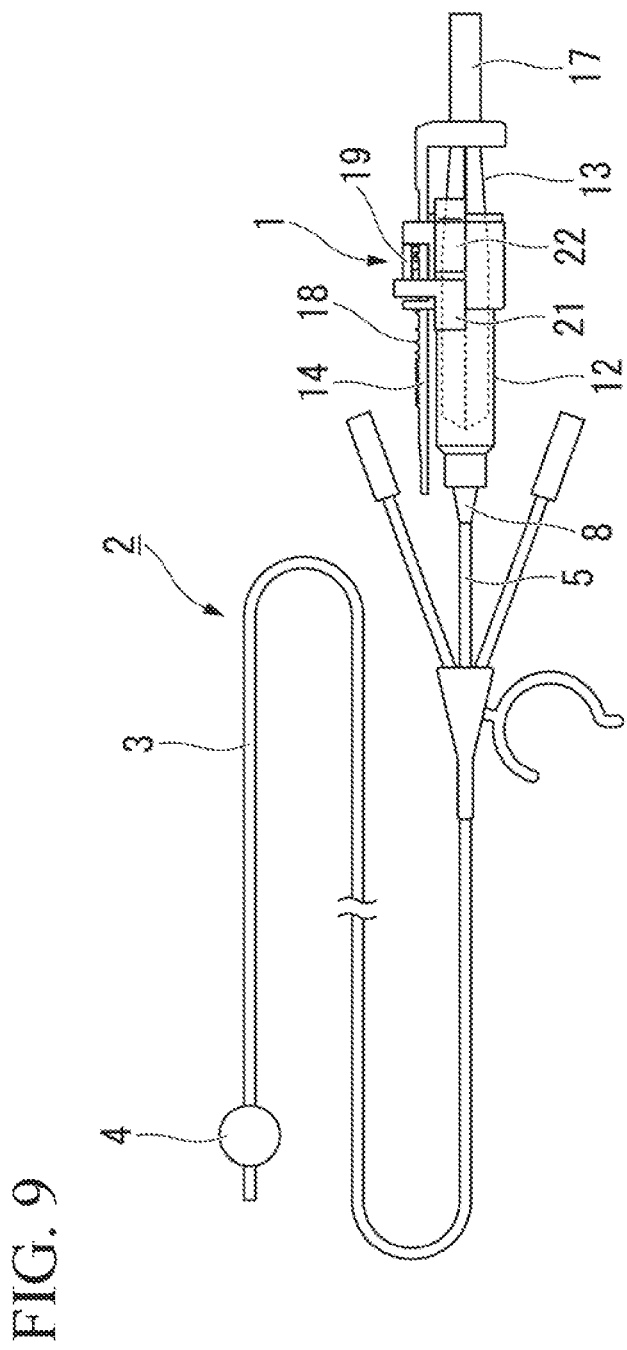
FIG. 9 is a view showing a state where the balloon is inflated.

Subsequently, as shown in FIG. 8, the plunger 13 is relatively advanced within the cylinder 12 so as to pull the cylinder 12. The projection 19A of the engaged portion 19 moves toward an engaging projection 18 closer to the proximal end side while riding over the engaging projections 18 of the adjusting portion 14 sequentially. Along with this, the fluid within the cylinder 12 is pushed out by the plunger 13 and supplied into the balloon 4 through the first port 8 and the first lumen 5 (refer to FIG. 9), and as shown in FIG. 9, the balloon 4 is inflated (balloon diameter inflation step).

If the user stops the advance operation of the plunger 13, the balloon 4 is deflated, and a force to push the fluid back to the cylinder 12 is applied to the plunger 13. Then, the engaging projections 18 of the adjusting portion 14 move to the proximal end side. Then, the inclined surface on the proximal end side of an engaging projection 18 that is closer to the distal end side than the projection 19A and is nearest to the projection 19A, and the inclined surface of the projection 19A on the distal end side come into contact with each other, and the plunger 13 comes to rest. In this way, the movement amount of the plunger 13 is uniformly maintained, and the size of the balloon 4 is reliably controlled and maintained at a diameter corresponding to the movement amount.

Figure 10:
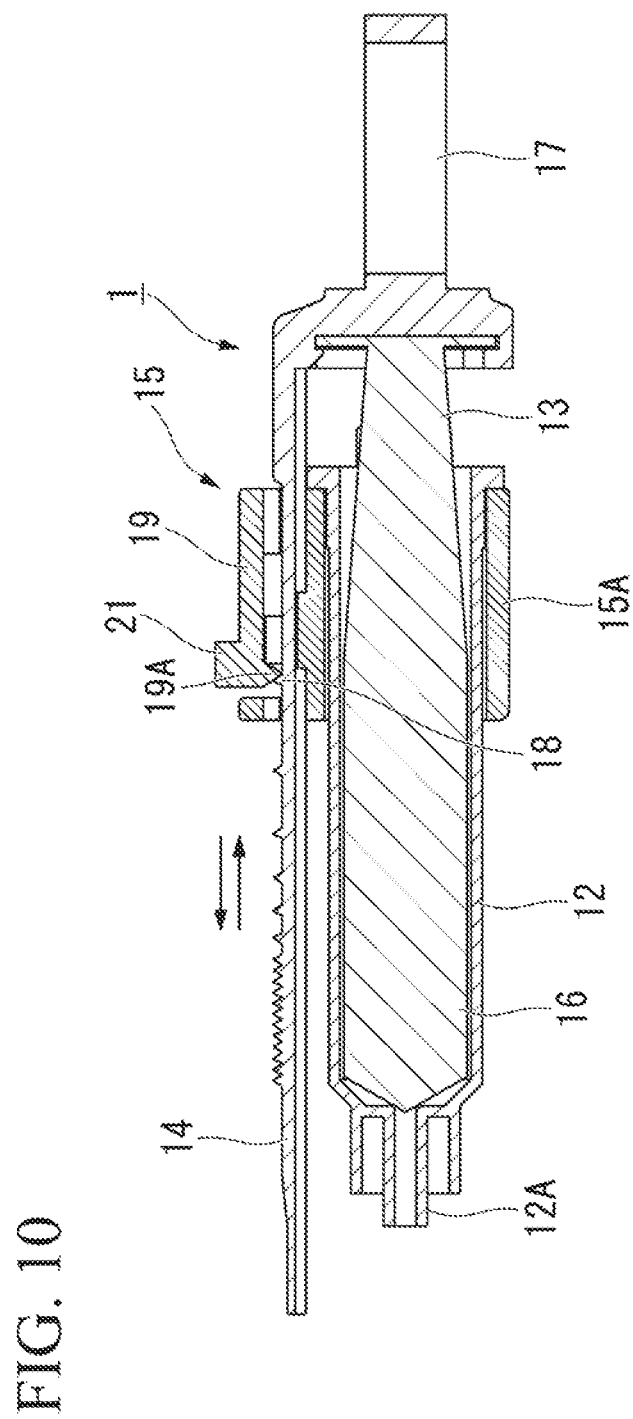
FIG. 10 is a view showing a state where an adjusting portion and a engaged portion are engaged with each other.
Figure 13B:
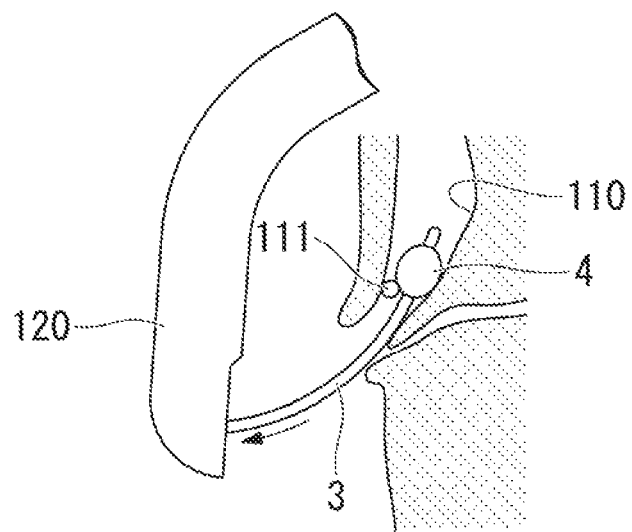
FIG. 13B is a view showing a state where the balloon is deflated in order to take a gallstone out of a bile duct in the vicinity of a bile duct outlet.

As shown in FIG. 10, when the diameter of the balloon 4 is changed, the plunger 13 is advanced and retracted with respect to the cylinder 12 by the above-described operation. For example, as shown in FIG. 13B, the diameter of the balloon 4 may be gradually reduced according to the internal diameter of the bile duct 110. By engaging the projection 19A of the fixing portion 15 with an engaging projection 18 at an arbitrary position, the movement amount of the plunger 13 is specified corresponding to the engaging projection 18, and the diameter of the balloon 4 (refer to FIG. 9) changes corresponding to the movement amount.

At this time, an operation in a direction in which the plunger 13 is pushed into a cylinder 12 is performed by user's action of closing his/her hand, and an operation in a direction in which the plunger 13 is pulled out of the cylinder 12 is performed by user's action of opening his/her hand. Generally, since a force by which a person opens his/her hand is weaker than a force by which the person closes his/her hand. Therefore, the load to the user when the user opens his/her hand becomes higher than when the user closes it.

From this perspective, in the balloon catheter 2 of the present embodiment, the force required when the user opens his/her hand in order to pull the plunger 13 out of the cylinder 12 is made smaller than the force required when the user closes his/her hand in order to push the plunger 13 into the cylinder 12.

Figure 11:
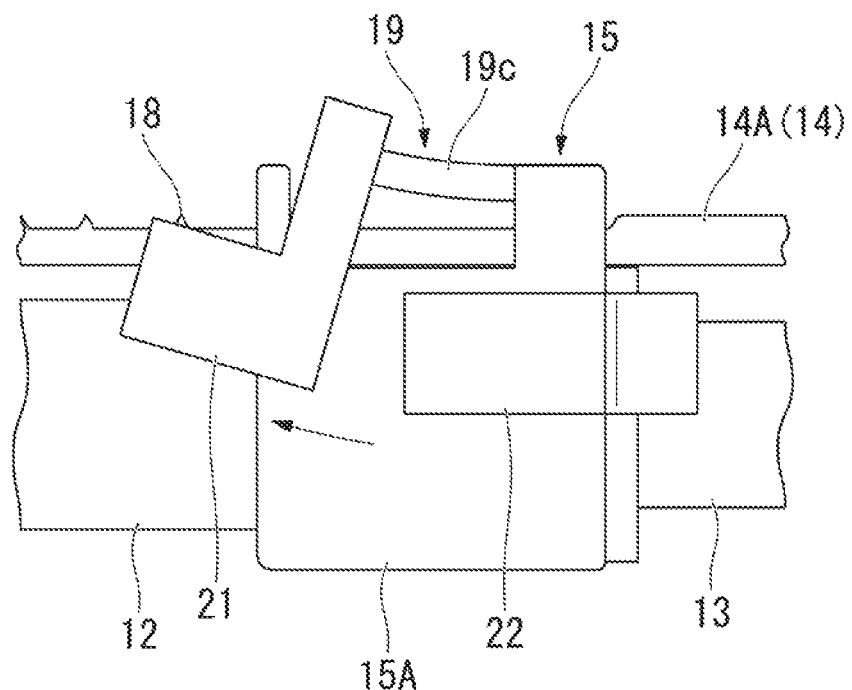
FIG. 11 is a view showing the operation of releasing the engagement between the adjusting portion and the engaged portion.

Specifically, if the user opens his/her hand in a state where the user passes his/her thumb through the grip 17 and passes his/her index finger and middle finger through the first finger-hooked portion 21 and the second finger-hooked portion 22 provided at the fixing portion 15, the first finger-hooked portion 21, as shown in FIG. 11, is pushed to the front side by the user's index finger and middle finger.

Figure 12:
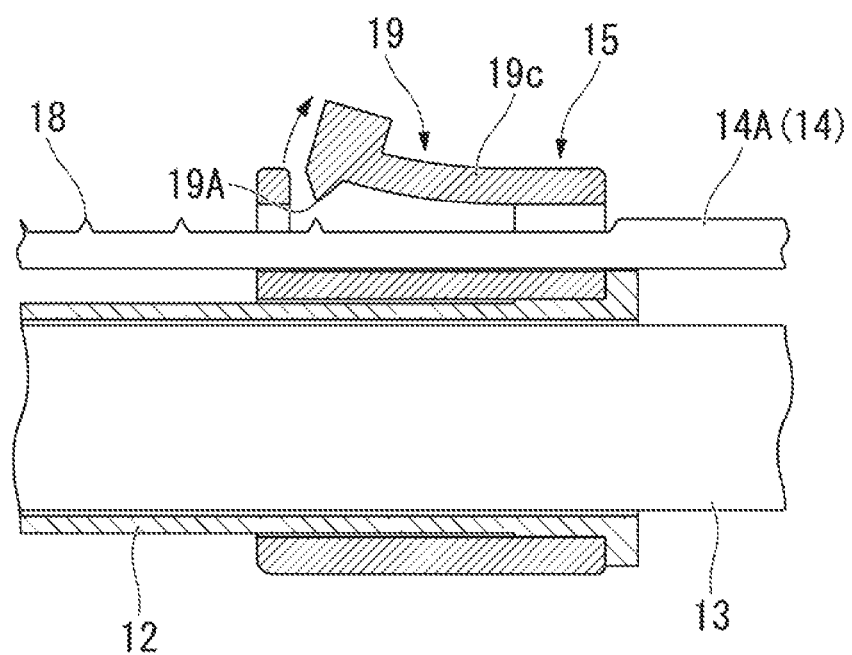
FIG. 12 is a view showing the operation of releasing the engagement between the adjusting portion and the engaged portion.

Since the first finger-hooked portion 21 is fixed to the distal end of the flat spring portion 19C, the first finger-hooked portion 21 moves to the front side and moves so as to approach the adjusting portion 14, by a force applied to the first finger-hooked portion 21 in order to relatively advance and retract the adjusting portion 14 and the fixing portion 15. Thereby, as shown in FIG. 12, the flat spring portion 19C to which the first finger-hooked portion 21 is fixed bends in a direction away from the central axis O2 of the plunger 13. If the flat spring portion 19C bends in the direction away from the central axis O2 of the plunger 13, the distal end of the flat spring portion 19C move in a direction away from the engaging projections 18 formed on the shaft portion 14A of the adjusting portion 14. That is, the projection 19A formed on the distal end of the flat spring portion 19C moves in the direction away from the engaging projections 18. This releases the engagement state of the engaged portion 19 with respect to an engaging projection 18. In addition, there is a case in which the engagement state of the engaged portion 19 with respect to the engaging projection 18 may not be completely released depending on the magnitude of a force that the user applies to the first finger-hooked portion 21. In this case, the projection 19A rides over the engaging projection 18 in a state where the projection 19A comes into slightly contact with the engaging projection 18, and a click feeling or sound can be transmitted to the user. That is, in a case where the balloon 4 is intended to be slightly deflated, the increase or decrease of the force and the amount how much a user's hand is opened can be adjusted while referring to a click feeling or sound when the projection 19A rides over the engaging projection 18. For this reason, the inflation diameter of the balloon 4 can be finely adjusted with keeping user's eyes on an image of the balloon 4 seen via the endoscope.

Additionally, when the user interrupts the action of opening his/her hand, the flat spring portion 19C is restored to the straight plate shape, and the projection 19A moves to the engaging projection 18 side. Thereby, the projection 19A is engaged with the engaging projection 18. As a result, the diameter of the balloon 4 is maintained.

In addition, if tire plunger 13 is quickly retracted and the projection 19A of the fixing portion 15 and the engaging projection 18 are engaged with each other at that position so as to bring the inside of the cylinder 12 into a negative pressure state, the balloon 4 can be more rapidly deflated (balloon diameter adjustment step).

When deflating the balloon 4 completely, the user opens his/her hand of which the fingers are passed through the first finger-hooked portion 21 and the second finger-hooked portion 22, with a stronger force. Thereby, the engagement state between the projection 19A and the engaging projection 18 is completely released, so that the plunger 13 and the cylinder 12 can move relatively and smoothly. For this reason, the plunger 13 is smoothly pulled out of the cylinder 12 simply by the user opening his/her hand.

In addition, since the fluid compressed within the balloon 4 tends to return to its original volume when the balloon. 4 is in an inflated state, the plunger 13 is pushed back by the deflation of the balloon 4.

According to the fluid supply body 1 of the present embodiment, the movement amount of the plunger 13 is specified by an engaging projection 18 provided on the adjusting portion 14, and the balloon 4 is inflated with a diameter corresponding to the movement amount. As the engaging projection 18 and the projection 19A of the fixing portion 15 engage each other, the inflation diameter of the balloon 4 is maintained. Accordingly, even in a range of a relatively smaller diameter such as the diameter fluctuates greatly with a smaller amount of movement of the plungers 13, the diameter control of the balloon can be exactly performed. In such a case, since the engagement state between the engaging projection 18 and the projection 19A is temporarily released by user's action of opening his/her hand, the burden can be reduced when the user opens his/her hand and the plunger 13 and the cylinder 12 are moved relatively.

Moreover, as the user opens his/her hand, the user's fingers in a closing state become gradually straight, so the first finger-hooked portion 21 can be moved by using the second finger-hooked portion 22 as a supporting point. For this reason, the projection 19A is easily removed from the engaging projection 18.

Additionally, even when the engagement force between the fixing portion 15 and the adjusting portion 14 is made high in order to resist a force when the plunger 13 is pushed back by the internal pressure of the balloon 4, the engagement between the fixing portion 15 and the adjusting portion 14 can be weakened simply by operator's action of opening his/her hand. That is, the engagement between the fixing portion 15 and the adjusting portion 14 can be weakened by the natural action of the operator who tries to deflate the balloon 4, and another action for adjusting the engagement force is not required.

Additionally, since the distances between the respective engaging projections are set to become large as the movement amount of the plunger 13 becomes large, it is possible to conform the variations (differential variation) of the diameter of the balloon 4 that varies when an engaging projection 18 to engage the projection 19A of the engaged portion 19 is shifted to the distal end side or to the proximal end side by one. Accordingly, it is also easy to control the inflation diameter of the balloon 4 at regular intervals, for example, intervals of 1 mm, or the like.

Moreover, since a state where the balloon 4 is inflated with a desired diameter is maintained by the fixing portion 15, it is not necessary to provide a mechanism, such as a stopcock for preventing a backflow of the fluid to the cylinder 12, between the fluid supply body and the first port 8. Accordingly, by using the fluid supply body 1, the configuration of the balloon catheter 2 can be made simple and therefore it is possible to manufacture can be made possible at low cost.

Although an example in which the balloon catheter 2 is used after being inserted into the endoscope 120 has been described in the above embodiment, the balloon catheter may be used without being fixed to an endoscope in a case where a target procedure is performed without using the endoscope.

Modified Examples 1 to 3

Next, modified examples 1 to 3 of the present embodiment will be described with reference to FIGS. 14 to 16. A difference between a fluid supply body 31 of the present embodiment and the fluid supply body 1 of the above-described first embodiment is the shape of the adjusting portion 14.

In addition, the same constituent elements as those of the above-described first embodiment will be designated by the same reference numerals, and a duplicate description will be omitted here.

Figure 14:
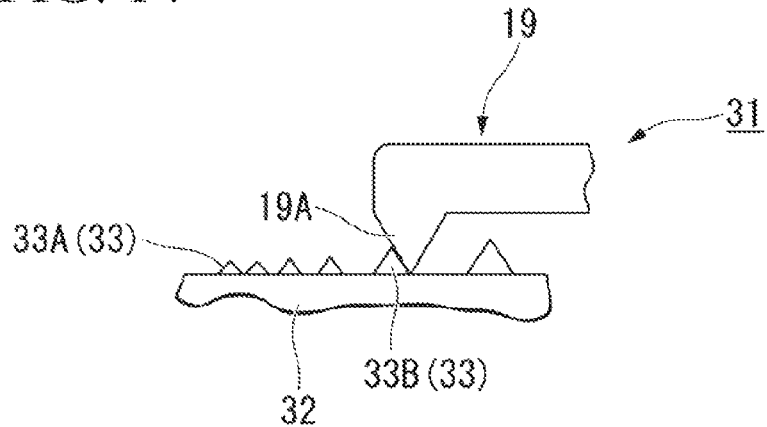
FIG. 14 is an enlarged view showing an adjusting portion and the engaged portion in a modified example 1 of the first embodiment.

FIG. 14 is an enlarged view showing an adjusting portion 32 and the engaged portion 19, of the fluid supply body 31 of modified example 1 of the present embodiment. Engaging projections 33 formed on the adjusting portion 32 are different in size, respectively, and an engaging projection 33A on the distal end side is smaller than an engaging projection 33B on the proximal end side. In this way, the size of the respective engaging projections 33 is set so as to become larger as it goes to the proximal end side.

As the plunger 13 moves forward, the projection 19A of the engaged portion 19 engages an engaging projection 33 closer to the proximal end side. Then, a larger amount of fluid is supplied by the balloon 4 and the diameter of the balloon 4 becomes large. At this time, a tension generated in the balloon 4 also becomes large, and a force that acts in a direction in which the plunger 13 is retracted also becomes large with an increase in the diameter of the balloon.

In the fluid supply body 31 of the present embodiment, since the engaging projections of the adjusting portion 32 on the proximal end side are formed so as to be larger, an engagement force (a force required to ride over an engaging projection 33 with which the projection 19A comes into contact) generated between the projection 19A and an engaging projection 33 becomes larger as the movement amount of the plunger 13 increases.

Accordingly, even if the diameter of the balloon 4 increases and a larger force acts in the direction in which the plunger 13 is retracted from the cylinder 12, the positional relationship between the plunger 13 and the cylinder 12 can be reliably maintained against this force, and the diameter of the balloon 4 can be uniformly maintained.

Figure 15:
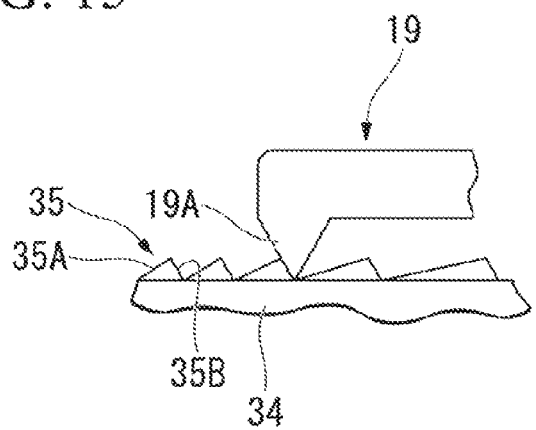
FIG. 15 is an enlarged view showing an adjusting portion and the engaged portion in a modified example 2 of the first embodiment.

FIG. 15 is an enlarged view showing an adjusting portion 34 of modified example 2 of the present embodiment. As shown in FIG. 15, the angle formed between a first inclined surface 35A of an engaging projection 35 on the distal end side and the bottom surface of the adjusting portion 34 parallel to the axis of the plunger 13 (that is, equal to an angle formed between the first inclination surface 35A and the axis of a plunger 13) is set to be smaller than a second inclined surface 35B of the engaging projection on the proximal end side. By providing such a configuration, the projection 19A can ride over an engaging projection 35 with a smaller force when the plunger 13 is advanced. Accordingly, the inflation operation of the balloon 4 can be facilitated while maintaining an advantage that the diameter of the balloon can be reliably controlled.

Figure 16:
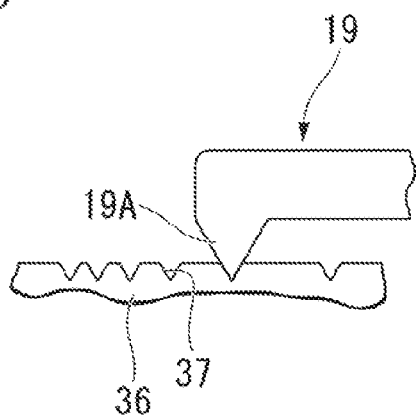
FIG. 16 is an enlarged view showing an adjusting portion and the engaged portion in a modified example 3 of the first embodiment.

FIG. 16 is an enlarged view showing an adjusting portion 36 of modified example 3 of the present embodiment. As in the modified example shown in FIG. 16, the shape of the adjusting portion 36 that engages the projection 19A of the engaged portion 19 may be formed as recessed portions 37. In this case, in order to increase engagement forces in the recessed portion 37 as the movement amount of the plunger 13 increases, the depth of the recessed portions 37 may be increased as it goes to the proximal end side of the adjusting portion 36. In addition, a recessed portion may be provided in the engaged portion, and the fixing portion may be configured so as to engage an engaging projection of the adjusting portion, or the angled formed between the axis of the plunger and a first inclined surface and a second inclined surface of an recessed portion may be made different from each other as in the above-described modified example 2.

Second Embodiment

Next, a second embodiment of the present invention will be described with reference to FIGS. 17 and 18.

Figure 17:
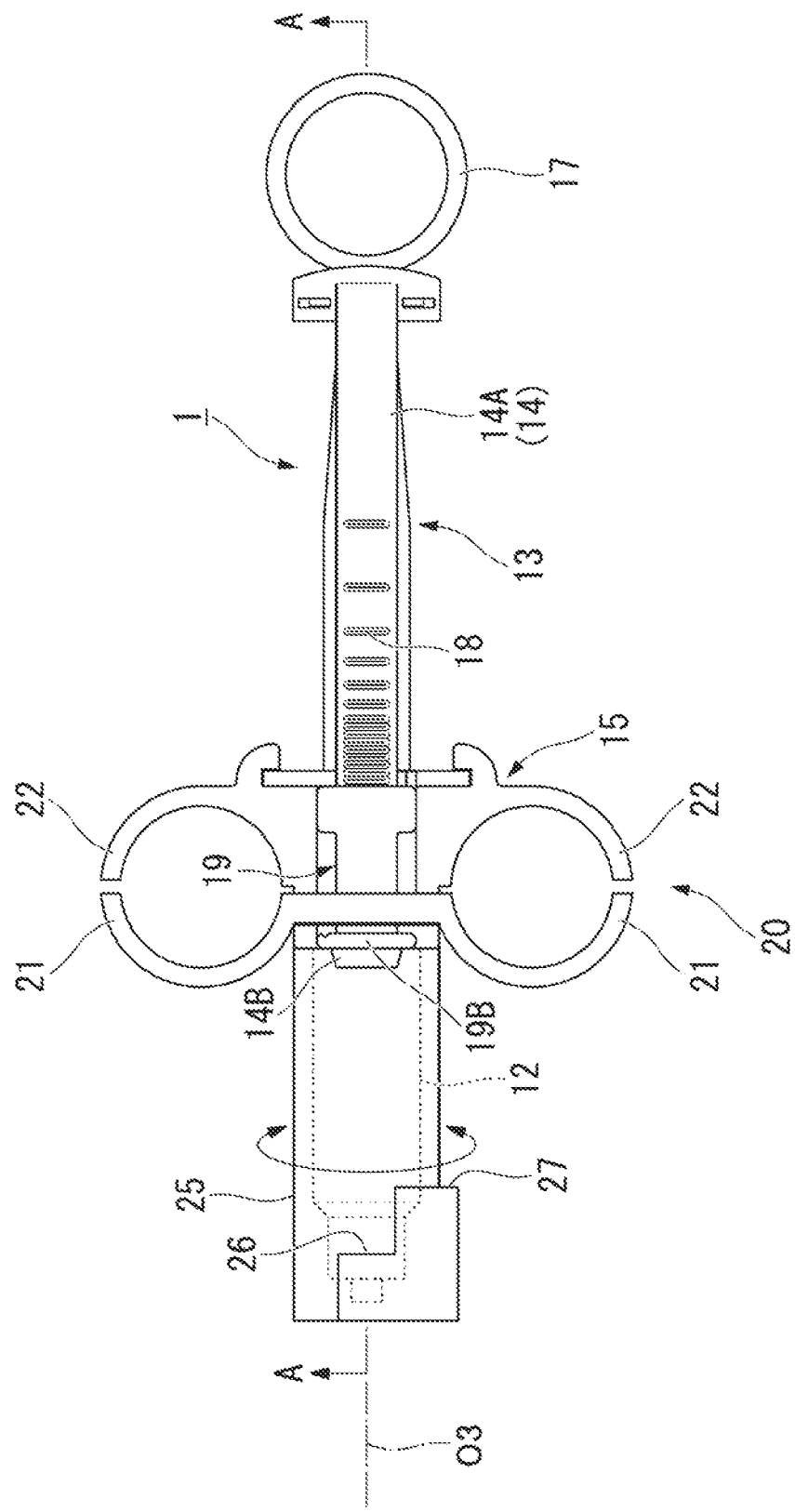
FIG. 17 is a plan view showing a fluid supply body of a second embodiment of the present invention.
Figure 18A:
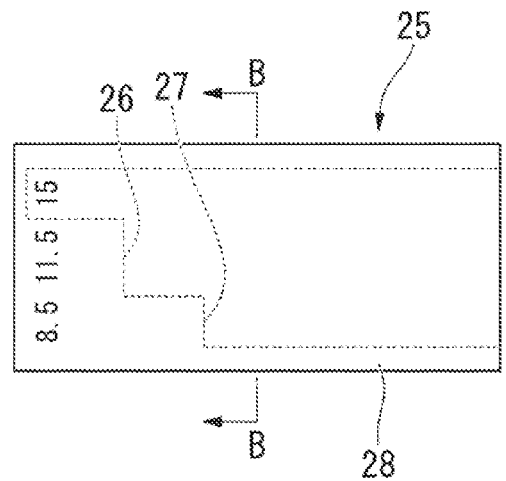
FIG. 18A is a side view showing another configuration example of a stopper in the fluid supply body of the embodiment.

FIG. 17 is a plan view of a fluid supply body of the present embodiment. FIG. 18A is a side view showing a stopper in the fluid supply body of the present embodiment, and FIG. 18B is a cross-sectional view in line B-B of FIG. 18A.

As shown in FIG. 17, in the present embodiment, a stopper 25 that rotates around the axis of the cylinder 12 is provided at the fixing portion 15.

The stopper 25 has two wall portions 26 and 27 that have mutually different positions in the direction of the axis of the cylinder 12 and spread in a planar direction perpendicular to the axis of the cylinder 12. A distal end of the shaft portion 14A in the adjusting portion 14 comes into contact with the respective wall portions 26 and 27. That is, the movement amount of the shaft portion 14A is regulated by the wall portions 26 and 27. The positions of the respective wall portions 26 and 27 correspond to the inflation diameter of the balloon 4. For example, the wall portion 27 on the proximal end side in the axial direction of the cylinder 12 is provided in order to regulate the inflation diameter of the balloon 4 to 8.5 mm, and the wall portion 26 on the distal end side in the axial direction of the cylinder 12 is provided in order to regulate the inflation diameter of the balloon 4 to 11.5 mm. Moreover, in a case where the shaft portion 14A does not come into contact with both the wall portions 26 and 27, the balloon 4 has a maximum inflation diameter (15 mm in the present embodiment) specified by the volume of the cylinder 12. In addition, the relationship between the arrangement of the respective wall portions 26 and 27 and the inflation diameter of the balloon 4 is an example, and in order to set the diameter of the balloon 4 to diameters other than the above-described inflation diameter, the position and number of wall portions are appropriately set. In the present embodiment the respective wall portions 26 and 27 formed at the stopper 25 also rotate around the axis O3 of the cylinder 12 by rotating the stopper 25 around the axis O3 of the cylinder 12. Thereby, a user can arbitrarily change and set the wall portions 26 and 27 capable of coming into contact with the distal end of the shaft portion 14A.

Figure 18B:
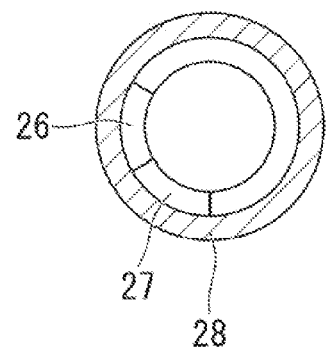
FIG. 18B is a cross-sectional view in line B-B of FIG. 18A.

In addition, as shown in FIGS. 18A and 18B, a cylindrical shell 28 surrounding the wall portions 26 and 27 may be provided if necessary. Additionally, in this case, it is preferable that marks indicating the positions of the respective wall portions 26 and 27 be provided at the shell 28. The marks provided at the shell 28, for example, can be provided by expressing the inflation diameters of the balloon 4 corresponding to the respective wall portions 26 and 27 in figures. The marks may be formed by printing, embossing, or the like.

As described above, in the present embodiment, the inflation diameter of the balloon 4 is specified as the adjusting portion 14 comes into contact with die respective wall portions 26 and 27. Thereby, when the diameter of the balloon 4 is adjusted to a desired size, the inflation diameter of the balloon 4 can be set to a suitable diameter while the operator watches an endoscope image or an X-ray image without seeing the operator's hand.

Additionally, even in a case where it is difficult to appropriately determine the inflation diameter of the balloon 4 from the endoscope image or the X-ray image, the inflation diameters of the respective wall portions 26 and 27 can be set to suitable diameters.

Modified Example 4

Figure 19:
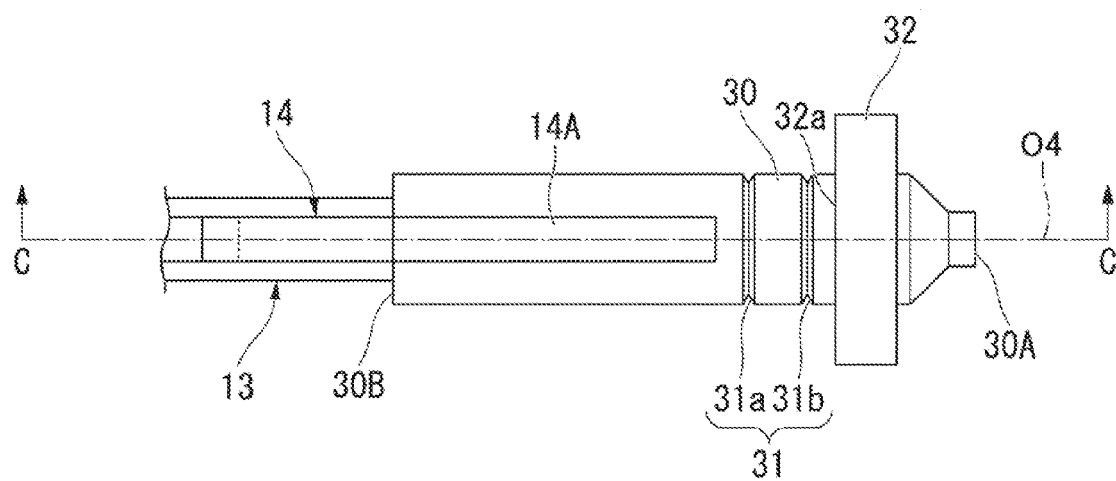
FIG. 19 is a plan view showing the configuration of a modified example 4 of the second embodiment.
Figure 20:
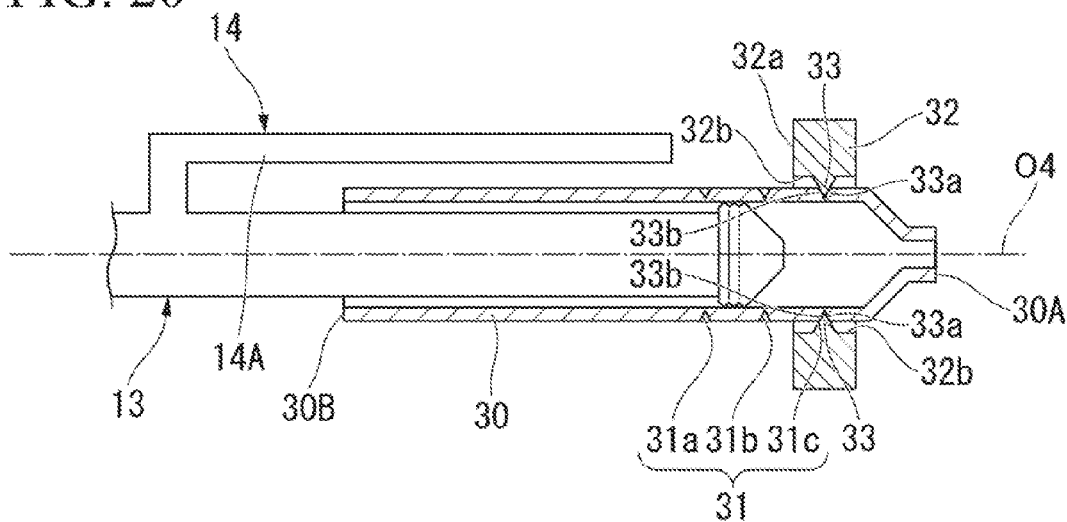
FIG. 20 is a cross-sectional view in line C-C of FIG. 19.

Next, a modified example 4 of the present embodiment will be described. FIG. 19 is a plan view showing the configuration of the present modified example 4. FIG. 20 is a cross-sectional view in line C-C of FIG. 19.

As shown in FIGS. 19 and 20, the present modified example is different from the configuration of the above-described second embodiment in that a cylinder 30 and a stopper 32 are provided instead of the stopper 25.

In the cylinder 30, a first end portion 30A on the distal end side and a second end portion 30B on the proximal end side open. The first end portion 30A fits to the first port 8 shown in FIG. 1. The plunger 13 can be inserted into the second end portion 30B. Although not shown, the cylinder 30 has the same configuration as the fixing portion 15 described in the first embodiment.

A groove 31 that extends in the circumferential direction of the cylinder 30 is provided on an outer peripheral surface of the cylinder 30. The groove 31 has a plurality of grooves (a first groove 31a, a second groove 31b, and a third groove 31c) that are spaced apart from each other in the direction of a central axis O4 of the cylinder 30.

The stopper 32 is an annular member formed with a through hole through which the cylinder 30 is inserted. A surface 32a of the external surfaces of the stopper 32 facing to the proximal end of the cylinder 30 is capable of coming into contact with the distal end of the shaft portion 14A in the adjusting portion 14, and regulates the movement amount of the shaft portion 14A, similar to the respective wall portions 26 and 27 in the above-described second embodiment. Additionally, the projection 33 that fits into the groove 31 formed in the outer peripheral surface of the cylinder 30 is formed on an inner peripheral surface 32b of the stopper 32 that is formed in an annular shape. Although the shape of the projection 33 is not particularly limited, for example, the projection 33 has a projecting strip shape that extends along the groove 31 formed in the outer peripheral surface of the cylinder 30.

Additionally, a surface 33a of the projection 33 on the distal end side is formed as an inclined surface that goes to the distal end side of the cylinder 30 as it goes to the radial outward side of the stopper 32 in a state where the stopper 32 is attached to the cylinder 30. Moreover, a surface 33b of the projection 33 on the proximal end side is formed as an inclined surface that goes to the proximal end side of the cylinder 30 as it goes to the radial outward side of the stopper 32 in a state where the stopper 32 is attached to the cylinder 30.

At least any one of the cylinder 30 and a stopper 32 is elastically deformable. In the present embodiment, the stopper 32 is more flexible than the cylinder 30, and as the stopper 32 is deformed, the projection 33 comes off the groove 31.

In the present modified example, the first groove 31a, the second groove 31b, and the third groove 31c are positioned in relation to the inflation diameter of the balloon 4. The stopper 32 is positioned with respect to the cylinder 30 at a position where the projection 33 fits into any one of the first groove 31a, the second groove 31b, and the third groove 31c. Then, the adjusting portion 14 is positioned with respect to the cylinder 30 in a place where the distal end of the shall portion 14A in the adjusting portion 14 comes into contact with the stopper 32.

Even in such a configuration, the same effects as the above-described second embodiment are exhibited.

Modified Example 5

Figure 21:
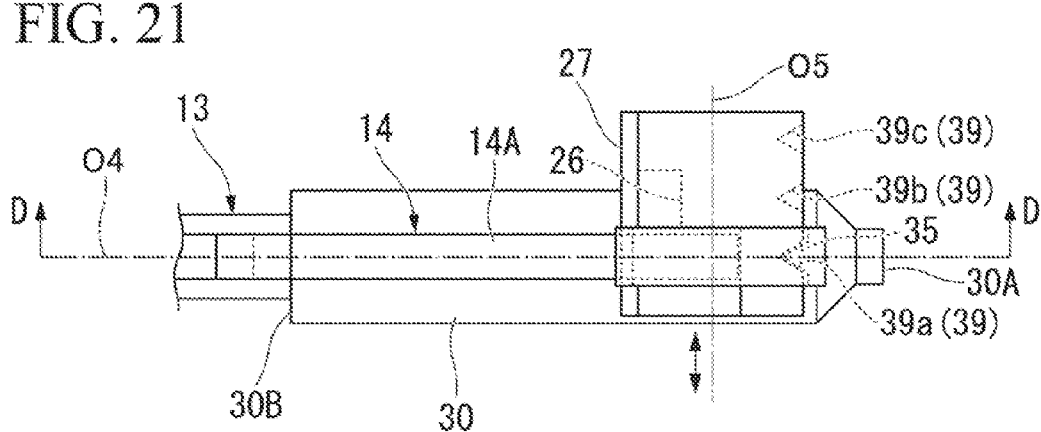
FIG. 21 is a plan view showing the configuration of modified example 5 of the second embodiment.
Figure 22:
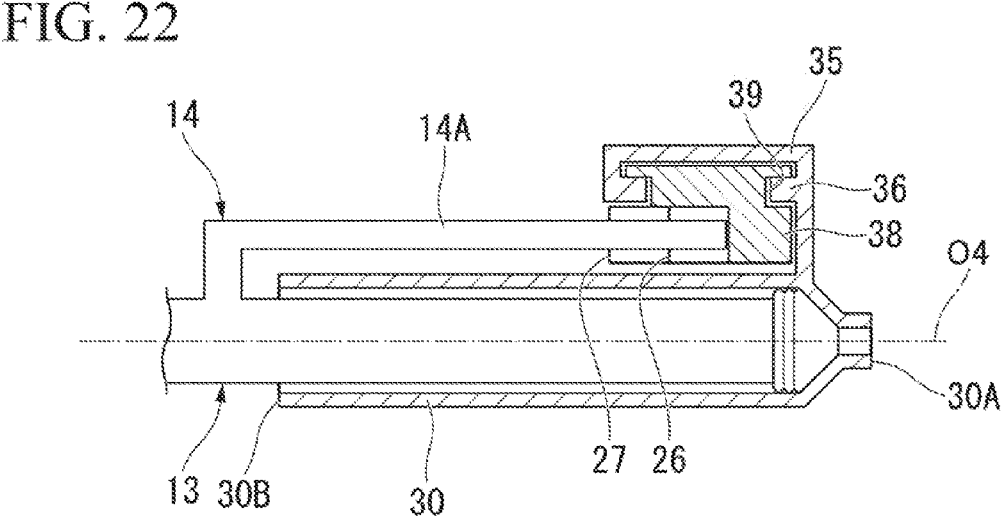
FIG. 22 is a cross-sectional view in line D-D of FIG. 21.

Next, modified example 5 of the above-described second embodiment will be described. FIG. 21 is a plan view showing the configuration of the present modified example. FIG. 22 is a cross-sectional view in line D-D of FIG. 21.

As shown in FIGS. 21 and 22, the present modified example is different from the above-described Modified Example 4 in that a stopper holding portion 35 is provided instead of the groove 31 and a stopper 38 is provided instead of the stopper 32.

The stopper holding portion 35 is formed at the outer peripheral surface of the cylinder 30, and holds the stopper 38 so that the stopper 38 is movable in the direction of a straight line O5 (in other words, the straight line O5 that has a direction vector perpendicular to the central axis O4 of the cylinder 30 and has a twisted position with respect to the central axis) that extends parallel to a straight line perpendicular to the central axis O4 of the cylinder 30.

Moreover, the stopper holding portion 35 has a projection 36 that engages the stopper 38 in order to hold the stopper 38 at a predetermined position.

The stopper 38 is formed with a plurality of recessed portions 39 (a first recessed portion 39a, a second recessed portion 39b, and a third recessed portion 39c) into which the projection 36 formed on the stopper holding portion 35 fits. Moreover, the stopper 38 is provided with the respective wall portions 26 and 27 described in the above-described second embodiment.

Even in such a configuration, the same effects as the above-described second embodiment and its modified examples 4 to 5 are exhibited.

In addition, as shown in the above-described second embodiment and its respective modified examples, the stopper for regulating the position of the distal end of the shaft portion 14A in the adjusting portion 14 may move in the circumferential direction (second embodiment) of the cylinder, the direction (Modified Example 4) of the central axis of the cylinder, and in the direction (Modified Example 5) of the straight line having an angle with respect to the central axis of the cylinder.

Third Embodiment

Figure 23:
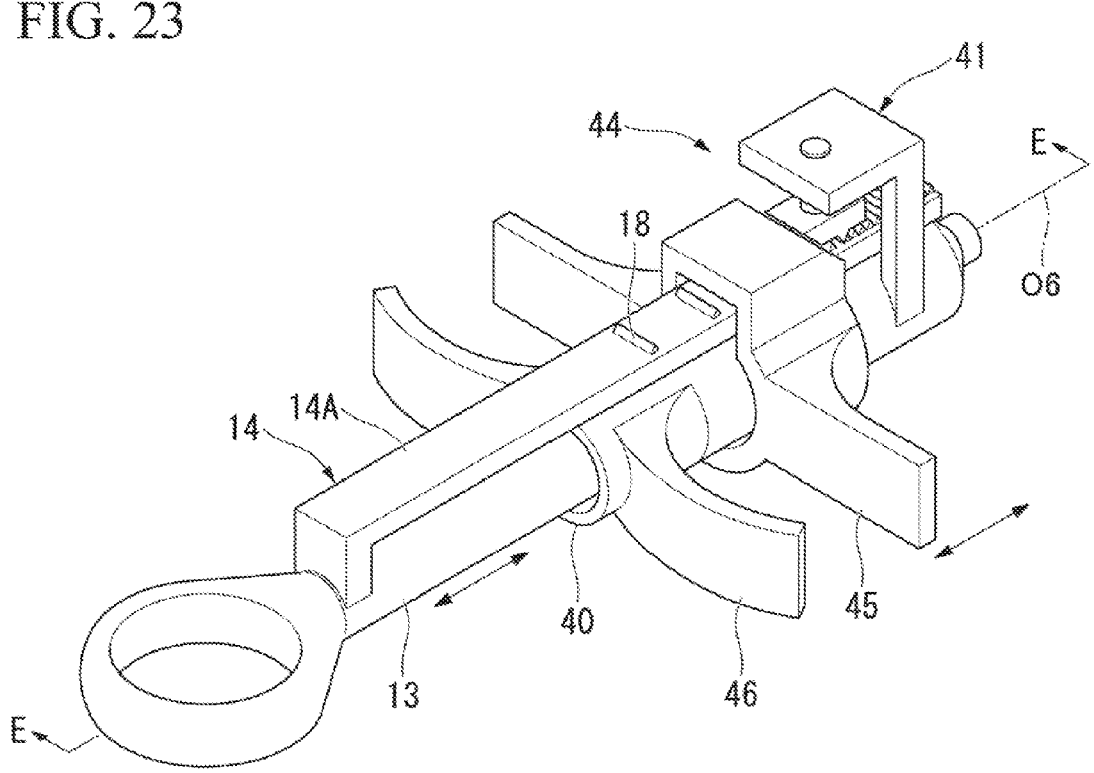
FIG. 23 is a perspective view showing a fluid supply body of a third embodiment of the present invention.
Figure 24:
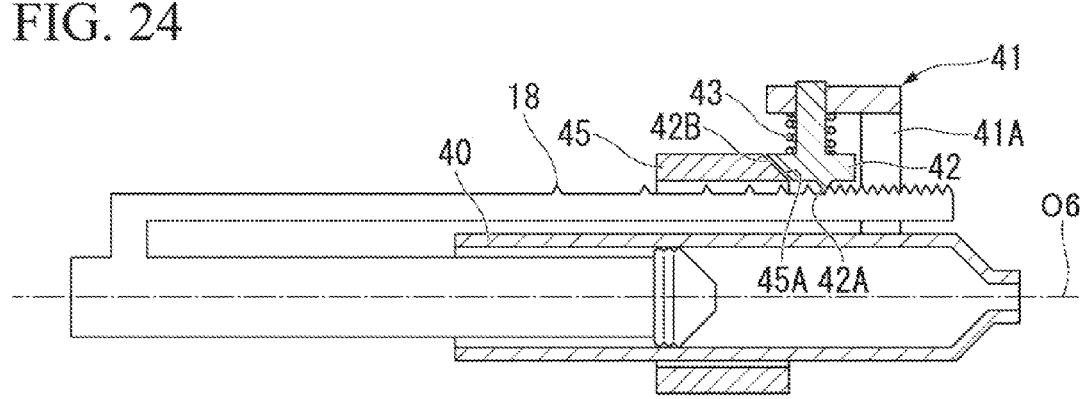
FIG. 24 is a cross-sectional view in line E-E of FIG. 23.
Figure 25:
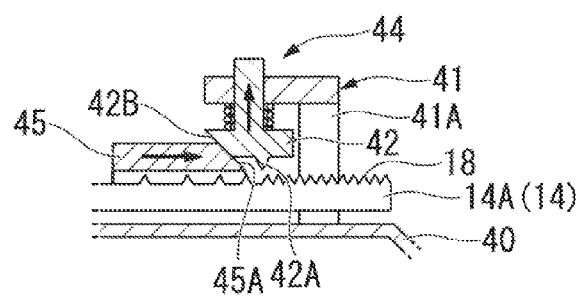
FIG. 25 is a view for describing the actions of the fluid supply body of the third embodiment.

Next, a third embodiment of the present invention will be described. FIG. 23 is a perspective view showing a fluid supply body of the present embodiment. FIG. 24 is a cross-sectional view in line E-E of FIG. 23. FIG. 25 is a view for describing the actions of the fluid supply body of the present embodiment.

As shown in FIGS. 23 and 24, the present embodiment is different in that a cylinder 40 is provided instead of the cylinder 12, a fixing portion 41 is provided instead of the fixing portion 15, and a converting portion 44 is provided instead of the converting portion 20.

The cylinder 40, which is a tubular member into which the plunger 13 described in the first embodiment can be inserted, and a fluid is contained in its inner cavity, similarly to the cylinder 12.

The fixing portion 41 has an engaged portion 42 that engages an engaging projection 18, similar to the engaged portion 19, an attaching portion 41A provided at the cylinder 40 in order to attach the engaged portion 42 to the cylinder 40, and a biasing member 43 that biases the engaged portion 42 toward the adjusting portion 14.

The engaged portion 42 has the same projection 42A as the projection 19A described in the first embodiment, and an inclined surface 42B having an angle with respect to a plane orthogonal to the central axis of the cylinder 40.

The converting portion 44 includes a finger-hooked portion 45 that is relatively disposed on the front side in the direction in which the plunger 13 is pushed into the cylinder 40, and a finger-hooked portion 46 that is relatively disposed on the rear side.

The finger-hooked portion 45 comes into contact with an operator's finger when the operator makes an action of opening his/her hand, similar to the first finger-hooked portion 21 in the above-described first embodiment. Unlike the first embodiment, the finger-hooked portion 45 is coupled to the cylinder 40 so as to be able to slightly advance and retract in the direction of a central axis O6 of the cylinder 40. Additionally, the finger-hooked portion 45 has an inclined surface 45A parallel to the inclined surface 42B formed on the engaged portion 42.

The finger-hooked portion 46 is fixed to an external surface of the cylinder 40 or is molded integrally with the cylinder 40. The finger-hooked portion 46 comes into contact with an operator's finger when the operator makes an action of closing his/her hand, similar to the second finger-hooked portion 22 described in the first embodiment.

In the present embodiment, as the operator makes an action of closing his/her hand, similar to the first embodiment in the process of inflating the balloon 4 (refer to FIG. 9), the operator's finger is apart from the finger-hooked portion 45, and the operator's finger is in contact with the finger-hooked portion 46. In this state, the finger-hooked portion 45 is moved to the proximal end side of the cylinder 40 by the biasing force of the biasing member 43. Moreover, the projection 42A is moved toward the adjusting portion 14 by the biasing force of the biasing member 43, and is engageable with an engaging projection 18. For this reason, in the process of inflating the balloon 4, a click feeling generated by the projection 42A riding over an engaging projection 18 can be obtained.

In an action of deflating the balloon 4, the finger-hooked portion 46 is pushed toward the distal end side of the cylinder 40 as the operator makes an action of opening his/her hand similar to in the first embodiment. Thereby, as shown in FIG. 25, the finger-hooked portion 46 moves to the distal end side of the cylinder 40, the inclined surface 45A comes into contact with the inclined surface 42B, the engaged portion 42 is pushed up by the finger-hooked portion 46, and the projection 42A separates from the engaging projection 18. Thereby, the operator can smoothly deflate the balloon 4 with a light force.

While preferred embodiments of the present invention have been described and illustrated above, it should be understood that these are exemplary of the present invention and are not limited to this. Additions, omissions, substitutions, and other modifications of constituents can be made without departing from the concept of the present invention.

For example, although an example in which the fluid supply body of the present invention is used for the balloon catheter has been described in the above-described respective embodiments, the application of the fluid supply body is not limited to this. For example, since the balloon can be easily controlled to a desired diameter if the fluid supply body of the present invention is used in an internal diameter measuring instrument or the like that inflates the balloon and inscribe the balloon in the internal diameter of a lumen and measures the internal diameter of the lumen, the measurement of the internal diameter can be smoothly performed.

Additionally, the first finger-hooked portion 21 described in the above-described first embodiment may be disposed at a portion of a side portion of the cylinder 12. Additionally, the first finger-hooked portion 21 may have only one semicircular arc portion.

In addition, the present invention is not limited by the above description and is limited only by the scope of the appended claims.

What is claimed is:

1. A fluid supply body for supplying a fluid to a balloon formed of a material having elasticity and inflating the balloon, the fluid supply body comprising:
    a cylinder that is a tubular shape having a first opening and a second opening at both ends thereof, and that contains the fluid;
    a plunger that is inserted into the cylinder from the second opening so as to be able to advance and retract in a direction of an axis of the cylinder and that pushes out the fluid which is in the cylinder from the first opening to the outside of the cylinder;
    an adjusting portion that is attached to the plunger and adjusts the movement amount of the plunger so that the balloon is inflated to a predetermined inflation diameter, the inflation diameter being changed as the balloon is inflated;
    a fixing portion that is provided at the cylinder and fixes the plunger at a position within the cylinder corresponding to the movement amount adjusted by the adjusting portion, the fixing portion including a first finger-hooked portion, and a second finger-hooked portion that is fixed to the cylinder;
    a plurality of engaging portions that are provided at the adjusting portion and specify movement amounts corresponding to a plurality of different inflation diameters of the balloon; and
    an engaged portion that is provided at the fixing portion, and is engaged with the engaging portions, wherein
        the first finger-hooked portion is disposed on a front side relative to the second finger-hooked portion in a direction in which the plunger is pushed into the cylinder, and is movable relative to the second finger-hooked portion, and
        the first finger-hooked portion moves relative to the second finger-hooked portion, and thereby the engagement of the engaging portions to the engaged portion is released.

2. The fluid supply body according to claim 1, wherein the fixing portion has:
    a flat spring portion that has the engaged portion formed at a first end of the flat spring portion and that has elasticity; and
    an attaching portion to which a second end of the flat spring portion is fixed and the cylinder is attached,
    the first finger-hooked portion is fixed to the first end side in the flat spring portion, and
    the second finger-hooked portion is fixed to the attaching portion.

3. The fluid supply body according to claim 2, wherein the first finger-hooked portion is disposed at a position apart from the axis in a direction perpendicular to the axis of the cylinder, and
    the flat spring portion is disposed at a position that is further apart from the first finger-hooked portion than to the axis.

4. The fluid supply body according to claim 2, wherein the second end of the flat spring portion, which is relatively located on the rear side in the direction in which the plunger is pushed into the cylinder, is fixed to the attaching portion, and extends to the front side in the direction in which the plunger is pushed into the cylinder, and the engaged portion is formed on the first end of the flat spring portion on the front side.

5. The fluid supply body according to claim 1, wherein the adjusting portion has:
    a shaft portion that extends parallel to the axis of the cylinder and at which the plurality of engaging portions are provided;
    a coupling portion that couples the shaft portion and the plunger; and
    a ring portion that is provided at the coupling portion,
    the fixing portion has:

a tubular attaching portion to which the cylinder is attached; and a stopper that is attached to the attaching portion, rotates around the axis of the cylinder, and has a plurality of wall portions that comes into contact with the end portion of the shaft portion, and the plurality of wall portions are positioned at mutually different positions in the direction of the axis of the cylinder, and are arranged side by side in a circumferential direction of the cylinder.

6. A balloon catheter having a balloon formed of a material having elasticity, comprising the fluid supply body according to claim 1.

7. A fluid supply body for supplying a fluid to a balloon formed of a material having elasticity and inflating the balloon, the fluid supply body comprising:

a cylinder that is formed in a tubular shape having a first opening and a second opening at both ends thereof, and that contains the fluid;

a plunger that is inserted into the cylinder from the second opening so as to be able to advance and retract in a direction of an axis of the cylinder and that pushes out the fluid which is in the cylinder from the first opening to the outside of the cylinder;

an adjusting portion that is attached to the plunger and adjusts the movement amount of the plunger so that the balloon is inflated with a predetermined inflation diameter, the inflation diameter being changed as the balloon is inflated;

a fixing portion that is provided at the cylinder and fixes the plunger at a position within the cylinder corresponding to the movement amount adjusted by the adjusting portion, the fixing portion including a first finger-hooked portion, and a second finger-hooked portion that is fixed to the cylinder;

a stopper that is provided in a state where a position of the stopper is fixed with respect to the cylinder and that is capable of coming into contact with the adjusting portion;

a plurality of engaging portions that are provided at the adjusting portion and specify movement amounts corresponding to a plurality of different inflation diameters of the balloon; and an engaged portion that is provided at the fixing portion, and is engaged with the engaging portions, wherein the first finger-hooked portion is disposed on a front side relative to the second finger-hooked portion in a direction in which the plunger is pushed into the cylinder, and is movable relative to the second finger-hooked portion; and the first finger-hooked portion moves relative to the second finger-hooked portion, and thereby the engagement of the engaging portions to the engaged portion is released.

8. The fluid supply body according to claim 7, wherein the adjusting portion has:

a shaft portion that extends parallel to the axis of the cylinder and at which the plurality of engaging portions are provided;

a coupling portion that couples the shaft portion and the plunger; and a ring portion that is provided at the coupling portion, the fixing portion has a tubular attaching portion to which the cylinder is attached;

the stopper is attached to the attaching portion, rotates around the axis of the cylinder, and has a plurality of wall portions that abut against the end portion of the shaft portion; and the plurality of wall portions are positioned at mutually different positions in the direction of the axis of the cylinder, and are arranged side by side in a circumferential direction of the cylinder.

\* \* \* \* \*